US009546939B2

(12) United States Patent
Liu et al.

(10) Patent No.: US 9,546,939 B2
(45) Date of Patent: Jan. 17, 2017

(54) INSPECTING DEVICE AND INSPECTING METHOD

(71) Applicant: Mitsubishi Electric Corporation, Chiyoda-ku (JP)

(72) Inventors: Zhengyong Liu, Tokyo (JP); Koji Shiratsuchi, Tokyo (JP); Rintaro Nagaoka, Tokyo (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 74 days.

(21) Appl. No.: 14/441,556

(22) PCT Filed: Nov. 25, 2013

(86) PCT No.: PCT/JP2013/081631
§ 371 (c)(1),
(2) Date: May 8, 2015

(87) PCT Pub. No.: WO2014/091913
PCT Pub. Date: Jun. 19, 2014

(65) Prior Publication Data
US 2015/0308933 A1    Oct. 29, 2015

(30) Foreign Application Priority Data

Dec. 11, 2012 (JP) ................................. 2012-270403

(51) Int. Cl.
*G01N 33/00* (2006.01)
*G01N 3/08* (2006.01)
(Continued)

(52) U.S. Cl.
CPC ............. *G01N 3/08* (2013.01); *G01M 5/0075* (2013.01); *G01N 3/00* (2013.01); *H01H 50/00* (2013.01);
(Continued)

(58) Field of Classification Search
None
See application file for complete search history.

(56) References Cited

FOREIGN PATENT DOCUMENTS

JP    61-80091 A    4/1986
JP    2001-33232 A    2/2001
(Continued)

OTHER PUBLICATIONS

International Search Report issued Dec. 24, 2013, in PCT/JP2013/081631, filed Nov. 25, 2013.

*Primary Examiner* — Robert R Raevis
(74) *Attorney, Agent, or Firm* — Oblon, McClelland, Maier & Neustadt, L.L.P.

(57) ABSTRACT

In a force waveform of an assembled body having an elastic component assembled thereto, in order to specify a deformation start point or a deformation end point of the elastic component as easily as possible, an inspecting device includes: a force-waveform detection system that applies a load to a workpiece having an elastic component in the direction of action of the elastic component and acquires a force waveform; an inspection-parameter designation unit that acts as reception unit in order to receive an input of an arbitrary designated point during a process of deformation; and an inspection unit that calculates a local slope of the force waveform at the designated point, thereby specifying, on the basis of the local slope at the calculated designated point, a physical characteristic change point including the deformation start point or the deformation end point.

7 Claims, 17 Drawing Sheets

(51) Int. Cl.
*G01N 3/00* (2006.01)
*H01H 50/00* (2006.01)
*G01M 5/00* (2006.01)

(52) U.S. Cl.
CPC ............... *G01N 2033/0078* (2013.01); *G01N 2203/0208* (2013.01); *G01N 2203/0288* (2013.01)

(56) References Cited

FOREIGN PATENT DOCUMENTS

| | | |
|---|---|---|
| JP | 2001-255238 A | 9/2001 |
| JP | 2012-57487 A | 3/2012 |
| JP | 2012-73182 A | 4/2012 |

INSPECTING DEVICE AND INSPECTING METHOD

FIELD

The present invention relates to an inspecting device and an inspecting method for inspecting the characteristics of an elastic component that is in a state of being assembled to an assembled body.

BACKGROUND

Conventionally, there is an inspecting method that applies a load (hereinafter, also "stress", "force", or "loading") to an elastic component by moving a hand driven by an external actuator with respect to an assembled body (hereinafter, "workpiece") having the elastic component assembled thereto so as to deform the elastic component. In this description, the elastic component refers to a component used as a generation source of a stress corresponding to the deformation. The elastic component includes, for example, a spring or rubber. According to the above inspecting method, the load applied to the elastic component and a travel distance of an end portion of the hand are detected; and the characteristics of the elastic component in a state with the elastic component being assembled to the workpiece are inspected on the basis of these detection values. As the characteristics of the workpiece to be inspected, for example, a force (a reaction force) or a modulus of elasticity generated in the assembled state can be mentioned.

For example, Patent Literature 1 discloses a core support plate plug inspecting device that measures a spring constant of a spring, which is a functional component of a core support plate plug. The core support plate plug inspecting device activates an actuator in a state with the spring being mounted on the core support plate plug, thereby pushing a piston (a hand) having a load cell at the end against the spring. The core support plate plug inspecting device detects a loading applied to the piston by the load cell; and detects a travel distance of the piston by a displacement meter. The core support plate plug inspecting device then calculates a spring constant of the spring mounted on the plug on the basis of these detection values. According to Patent Literature 1, it is supposed that, as a work of detaching the spring and the plug is not required, a work for confirming the soundness of the core support plate plug can be easily performed.

Patent Literature 2 discloses an inspection system that inspects a spring force and a spring constant in a state with a spring being assembled so as to be sandwiched between a pump body and a housing. The spring is assembled in a compressed state and is in a state of generating a spring force in an extending direction of the spring, among the directions of action of the spring. An externally threaded member is disposed at a predetermined position in the extending direction of the spring in the housing, and the most extending position of the spring in a range of movement of the pump body is restricted by the external thread member. In the inspection system, a piston driven by an actuator presses against the pump body so as to push the spring in a direction in which the spring in the direction of action of the spring force is compressed. The inspection system then calculates the spring constant on the basis of a loading generated by a pressing force and a measurement value of an end position of the pump body. The inspection system then obtains the spring force in an actual usage state on the basis of force information at a point where the external thread member is separated from the pump body (that is, a point where the force of the spring applied to the housing (a housing reaction force) becomes zero). According to Patent Literature 2, it is supposed that whether the actual spring force after assembly is within a set range can be determined.

CITATION LIST

Patent Literatures

Patent Literature 1: Japanese Patent Application Laid-open No. S61-080091
Patent Literature 2: Japanese Patent Application Laid-open No. 2001-255238

SUMMARY

Technical Problem

When the characteristics of the elastic component are to be calculated, it becomes necessary to specify a detection value in a state with the elastic component being in a process of deformation on the basis of a detection value of a loading applied to the hand and a detection value of the travel distance of the hand.

Meanwhile, a deformation start point and a deformation end point of the elastic component are not always unchanged due to a positioning error of the workpiece and a dimension error of other components disposed around the elastic component. Therefore, the deformation start point and the deformation end point of the elastic component need to be designated for every inspecting operation.

For example, according to the technique disclosed in Patent Literature 1, when the piston is brought down by activating the actuator, a point where the load cell at the end of the piston contacts a shaft varies, due to variations in the length of the shaft that are deformed corresponding to the deformation of the spring. That is, in information of the loading applied to the piston, which is acquired by the load cell, a start point of the reaction force of the spring is not constant. In this case, if a start point and an end point of a deformation section of the spring are set in advance, reaction force information between the start point and the end point changes for each operation; and thus there are variations in calculation results. Further, information of the deformation section of components other than the spring may be included in the set deformation section, and thus correct calculation results of the spring constant may not be obtained. When calculating the spring constant accurately, information of a period, during which the piston is brought into contact with the shaft, is cut out from the information of the travel distance of the piston. Therefore, it is required to designate a point where the piston comes into contact with the shaft for each inspecting operation, thereby causing problems of low productivity and high production costs.

Furthermore, the objective of the technique described in Patent Literature 1 is to confirm the soundness of a core support plate plug. In other words, the object is to confirm whether the reaction force of a spring can endure a pressure difference between a lower part and an upper part of the core support plate plug in order to prevent the occurrence of any functional problem of the plug during the operation of a nuclear reactor. However, if there is a dimension error in the length of the shaft or deformation has occurred in the shaft or the plug, the compression amount of the spring changes. Therefore, even if it is found that the spring constant of the spring is the same, there are variations in the reaction force in the spring. As a result, a problem remains in which the robustness of the core support plate plug cannot be ensured.

Meanwhile, according to the technique disclosed in Patent Literature 2, in the inspection system, a pump body is pressed by a press device. The inspection system then calculates a spring constant on the basis of a force waveform describing a relation between a measured loading and a measurement amount of the end position of the pump body; and obtains the reaction force of the spring in the actual usage state on the basis of the calculated spring constant and the measurement value of the loading at a position where the reaction force of the housing becomes zero, thereby estimating the spring force in the assembled state. With this configuration, even if a set length of the spring changes due to a dimension error or deformation of peripheral components for sandwiching the spring therebetween, it can be confirmed whether the actual spring force at the time of actual usage is set within the set range.

However, according to the technique disclosed in Patent Literature 2, because it is necessary to specify the point where the housing reaction force on the acquired force waveform becomes zero (that is, a deformation start point), a device for detecting the housing reaction force needs to be prepared in the inspection system, and as a result, there is a problem that the cost required for the inspection system increases. In addition, according to the technique disclosed in Patent Literature 2, the deformation start point needs to be designated. However, if there is a dimension error in the peripheral components for sandwiching the spring therebetween, or the peripheral components deform, the deformation start point chances. Therefore, the operator needs to set the deformation start point for each inspecting operation. As long as the deformation start point is designated manually by the operator, there is a limitation on streamlining of the inspecting operation.

The present invention has been achieved in view of the above problems, and an objective of the present invention is to provide an inspecting device and an inspecting method for specifying a deformation start point or a deformation end point of an elastic component as easily as possible in a force waveform concerning an assembled body assembled thereto with the elastic component.

Solution to Problem

In order to solve the problem described above and achieve the objective, the present invention relates to an inspecting device that includes: a force-waveform detection system that applies a load to an assembled body having an elastic component assembled thereto in a direction of action of the elastic component and acquires a force waveform describing a relation between the load and an amount of displacement; a reception unit that receives an input of a designated point during a process of deformation of the elastic component in the force waveform acquired by the force-waveform detection system; and an inspection unit that calculates a local slope of the force waveform at the designated point, calculates a local slope at a focus point different from the designated point, and determines, on the basis of a comparison between the local slope at the focus point and the local slope at the designated point, whether the focus point is a change point of the force waveform. The inspection unit searches for a first focus point that first satisfies, on the basis of the local slope at the designated point and a first parameter, a first condition at least stating that the local slope at the first focus point reaches a first threshold, while moving the first focus point in a direction away from the designated point by using the designated point as a point of the starting, specifies the first focus point first satisfying the first condition as a first change point, searches for a second focus point that first satisfies, on the basis of a second parameter, a second condition at least stating that the local slope at the second focus point reaches the local slope at the designated point or is inside of a range between the local slope at the designated point and the slope, while moving the second focus point in a direction approaching the designated point by using the first change point as a point of the starting, and specifies the second focus point first satisfying the second condition as a second change point.

Advantageous Effects of Invention

According to the present invention, the inspecting device can specify a change point only by inputting a designated point, and thus the inspecting device can specify a deformation start point or a deformation end point of an elastic component as easily as possible.

DESCRIPTION OF EMBODIMENTS

Exemplary embodiments of an inspecting device and an inspecting method according to the present invention will be described below in detail with reference to the accompanying drawings. The present invention is not limited to the embodiments.

First Embodiment

Figure 1:
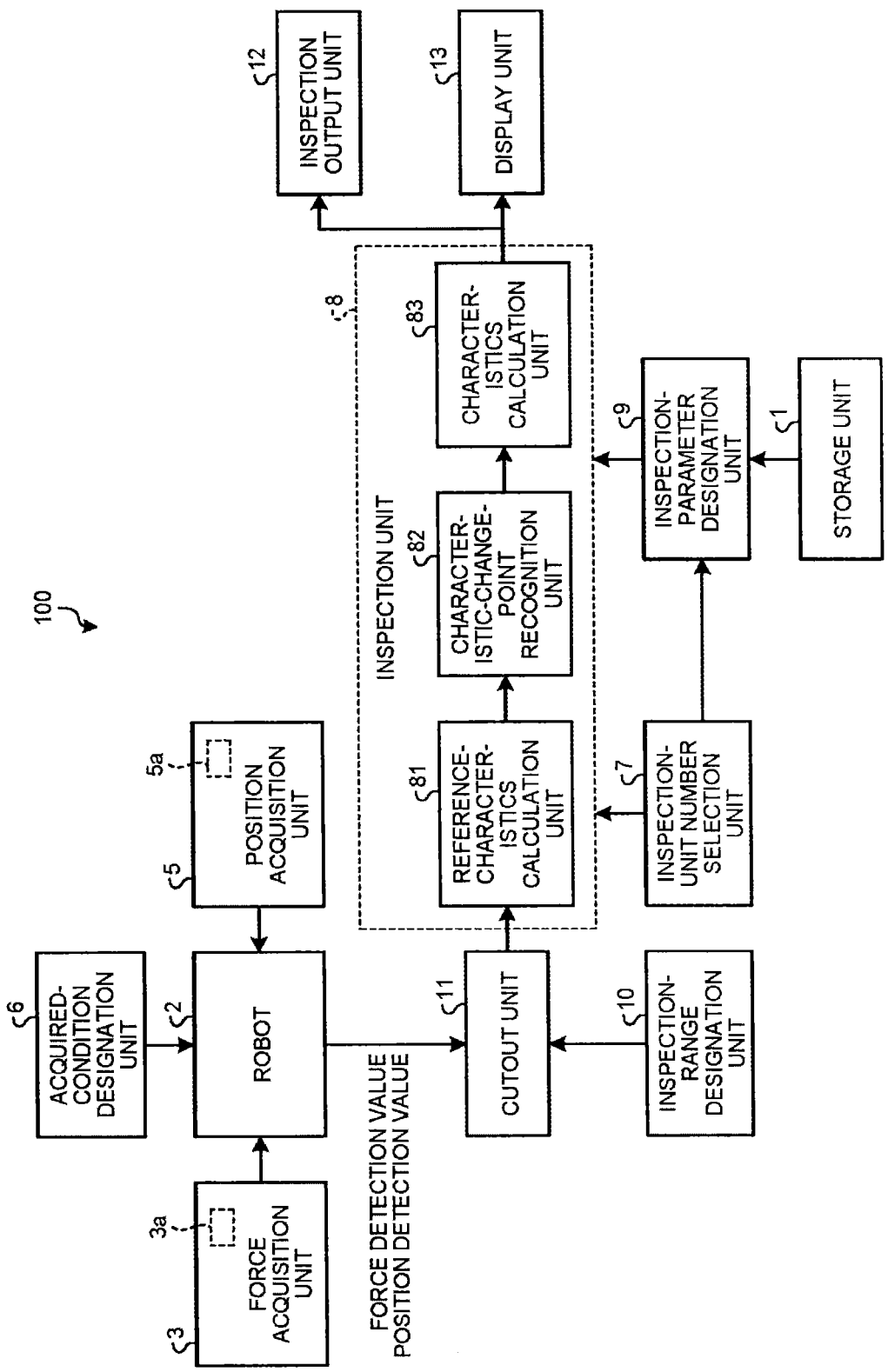
FIG. 1 is a diagram illustrating a configuration of an inspecting device according to a first embodiment of the present invention.

FIG. 1 is a diagram illustrating a configuration of an inspecting device according to a first embodiment of the present invention. An inspecting device 100 includes a robot 2; a force acquisition unit 3; a position acquisition unit 5; an acquired-condition designation unit 6; an inspection-unit number selection unit 7; an inspection-parameter designation unit 9; an inspection-range designation unit 10; a cutout unit 11; an inspection unit 8; an inspection output unit 12; and a display unit 13.

The robot 2, the force acquisition unit 3, and the position acquisition unit 5 function as a system for detecting the force-waveform in cooperation with each other. This force-waveform detection system can apply a load to an assembled body having an elastic component assembled thereto in a direction of action of the elastic component so as to acquire an aggregation of a pair of the load and an amount of displacement (hereinafter, the aggregation is referred to as "force waveform").

Figure 2:
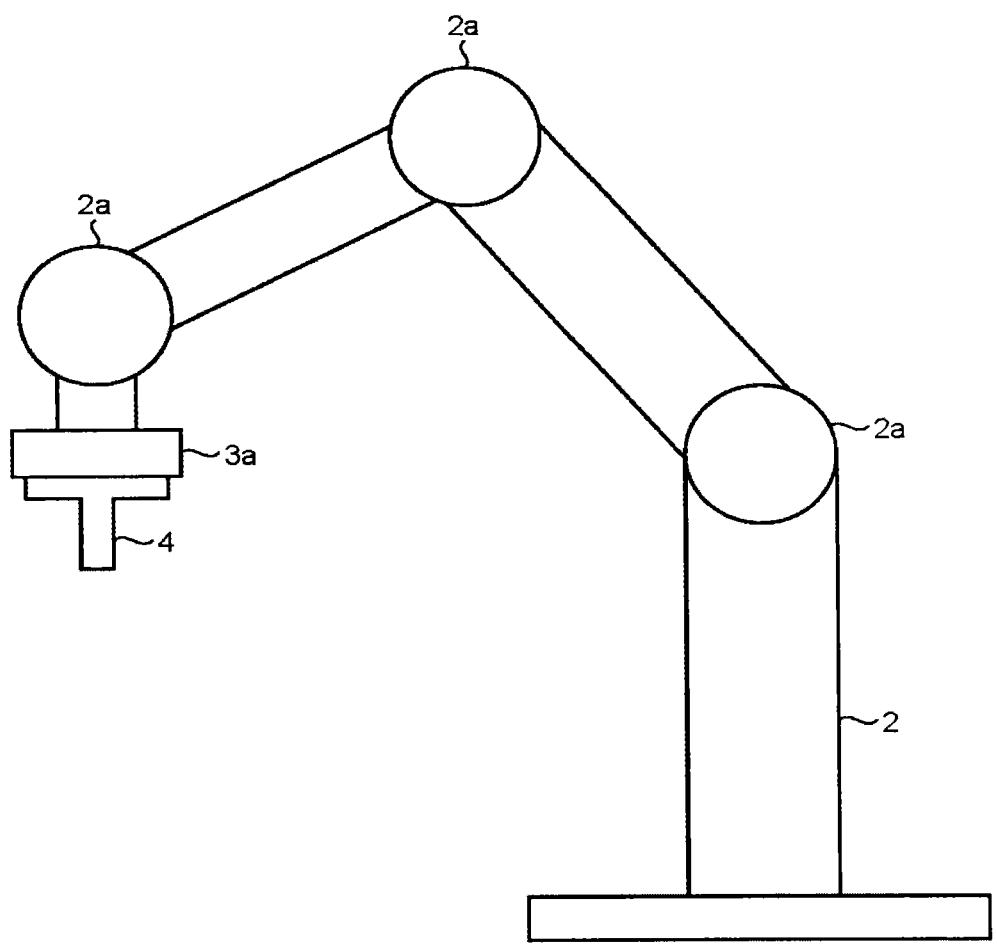
FIG. 2 is a diagram illustrating a configuration of a robot.

FIG. 2 is a diagram illustrating a configuration of the robot 2. The robot 2 is a vertical articulated robot having a motor 2a in a plurality of joints. The robot 2 includes a hand 4 near an end (at an end) via a force sensor 3a. The force sensor 3a can measure: force acting on each of a plurality of shafts each of which ends of the hand of the robot 2 is set as an origin; and a moment around the respective shafts. That is, the force sensor 3a can measure the force and moment acting on the hand 4. The hand 4 can be always provided at the end of the robot 2. Further, the robot 2 can be configured such that the robot 2 includes an opening/closing hand or a tool changer on the body side than the hand 4 of the robot 2, so that the hand 4 is held by the opening/closing hand or the hand 4 is fitted to the tool changer only during the inspecting operation. Note that the robot 2 can be such that it only performs an inspecting operation, or that it performs an inspecting operation during other operations such as transferring and assembling. Further, the robot 2, instead of being a vertical articulated robot, can be such that it is a scalar robot or an orthogonal robot in which all the shafts are configured by a direct drive shaft (a shaft operating in a straight line).

The inspecting device 100 drives the robot 2; pushes the hand 4 against the assembled body having the elastic component assembled thereto in a direction of deformation of the elastic component so as to apply a load; and measures the load and the amount of displacement in a pair, thereby being able to specify data at a deformation start point and a deformation end point of the elastic component in the force waveform.

The force acquisition unit 3 acquires a force acting on the hand 4 from the force sensor 3a. The force acquisition unit 3 sends the acquired force as a force detection value to the inspection unit 8 and the display unit 13 via the robot 2 and the cutout unit 11. When the force sensor 3a is a six-axis force sensor, the force detection value includes a force in three-axis directions and moments about the respective axes. When the force sensor 3a is a force sensor including five axes or less, the force detection value includes a force in three-axis directions and a moment that can be measured among the moments about the axes. The force sensor 3a is provided, for example, for each axis and for each moment in the force acquisition unit 3; and the respective force sensor 3a sends the force detection value respectively to the inspection unit 8 and the display unit 13.

The position acquisition unit 5 acquires the end position of the hand 4. Specifically, the position acquisition unit 5 is configured to include a position sensor 5a that measures the position of the motor 2a. The position sensor 5a corresponds to, for example, an encoder or a resolver. The position acquisition unit 5 detects the position of the motor 2a by using the position sensor 5a; and acquires coordinate transformation of the detected position of the motor 2a so as to calculates the end position of the robot 2 (the end position of the hand 4). The position acquisition unit 5 sends the acquired position to the inspection unit 8 and the display unit 13 via the robot 2 and the cutout unit 11, as the acquired position being the position detection value.

The acquired-condition designation unit 6 specifies a sampling period, the detection start point, and the detection end point regarding the force and position used by the force acquisition unit 3 and the position acquisition unit 5. The acquired-condition designation unit 6 executes designation on the basis of, for example, a command included in a robot program describing the operation of the robot 2. For example, the acquired-condition designation unit 6 executes designation on the basis of the following command.

FsTCond On, 1

Here, "FsTCond On" is a robot language (a command) for designating the detection start point, and "1" is a number designating the sampling period. For example, when the number is "1", the sampling period is 1.0 millisecond.

The acquired-condition designation unit 6 executes designation on the basis of the following command.

FsTest On, 30

In this case, "FaTest On" is a robot language (a command) for designating the detection start point, by using the percentage to a travel distance from the operation start point to the operation end point of the hand 4; and "30" means that a point of 30% from the start point of an assembly operation is designated as the detection start point.

The acquired-condition designation unit 6 executes designation on the basis of the following command.

FsTest Off, 50

In this case, "FsTest Off" is a robot language (a command) for designating the detection end point, by using the percentage to the travel distance from the operation start point to the operation end point of the hand 4; and "50" means that a point of 50% from the start point of the assembly operation is designated as the detection end point.

In the present embodiment, the percentage of the travel distance from the operation start point is used to designate the detection start point and the detection end point. However, the designation method is not limited thereto. The following, for example, can be used as the designation method: the percentage of the travel distance to the operation end point, the travel distance from the operation start point, the travel distance to the operation end point, or an elapsed time from operation start.

The inspection-unit number selection unit 7 specifies an axis to be inspected, and selects an inspection unit number according to the type of operation to be performed by the robot 2. The inspection unit number includes the number of designating the inspecting operation to be performed by the inspection unit 8. The inspection-unit number selection unit 7 also sends information of the axis to be inspected to the designated inspection unit 8, and sends the inspection unit number to the inspection-parameter designation unit 9. The inspection-unit number selection unit 7 specifies the axis to be inspected and selects the inspection unit number on the basis of the robot program or an input by an operator.

For example, when the operation to be performed by the robot 2 is to fit an electromagnetic switch, the inspection-unit number selection unit 7 selects "51" as the inspection unit number. When the operation to be performed by the robot 2 is an inspecting operation to measure a spring constant of a spring of the electromagnetic switch, the inspection-unit number selection unit 7 selects "52" as the inspection unit number.

For example, when the operation to be performed by the robot 2 is an inspecting operation to measure a spring constant of the spring, the inspection-unit number selection unit 7 performs selection of the inspection unit number and designation of the shaft by executing the following command in the robot program.

FsTAlgo, 52, 3

In this case, "FsTAlgo" is a robot language (a command) for designating the inspection unit number and the shaft, "52" indicates the inspection unit number, and "3" means that a Z-axis is designated as the axis to be inspected.

The inspection-parameter specification unit (reception unit) 9 receives the inspection unit number from the inspection-unit number selection unit 7. A storage unit 1 stores therein in advance a combination of the inspection parameters for each of the inspection unit number. The value of the inspection parameter is set in advance by, for example, an operator. The inspection-parameter designation unit 9 refers to the storage unit 1 in order to acquire the combination of the inspection parameters corresponding to the inspection unit number received from the inspection-unit number selection unit 7. The inspection-parameter designation unit 9 sends (sets) the acquired combination of the inspection parameters to the inspection unit 8. Details of the inspection parameter are described later.

According to the present embodiment, the inspection-parameter designation unit 9 acquires the inspection parameter corresponding to the inspection unit number and sets the inspection parameter. However, the present embodiment can be configured such that the combination of the inspection parameters is directly described in the robot program to be set.

The inspection-range designation unit 10 designates a range to be sent to the inspection unit 8 out of pairs of force/position detection values acquired for the section from the detection start point to the detection end point. That is, the inspection-range designation unit 10 designates an inspection range for specifying a physical characteristic change point (a change point) in the force waveform. Here, the physical characteristic change point refers to a point at which the slope changes in the force waveform. The deformation start point and the deformation end point both correspond to the physical characteristic change point. For example, when the inspection unit 8 is to measure the modulus of elasticity of the elastic component or force that is generated in a state with the elastic component being assembled, the deformation start point and the deformation end point need to be specified. In this case, the inspection-range designation unit 10 designates a section that has a sufficient range for specifying the deformation start point and the deformation end point, which includes all the sections from the deformation start point to the deformation end point of the elastic component. It is assumed, here, that a start point of the range designated by the inspection-range designation unit 10 is an inspection-process start point; and an end point thereof is an inspection-process end point. The inspection-process start point and the inspection-process end point are sent to the cutout unit 11.

The inspection-process start point and the inspection-process end point can be designated by an orthogonal coordinate position of the robot 2. In the present embodiment, in order to address a case in which the inspecting operations are repeated, the inspection-process start point and the inspection-process end point are designated by the percentage to a total travel distance, assuming that the total travel distance (obtained by accumulating an absolute value of the travel distance between pieces of position data on the designated axis) from the starting of the detected force waveform (the detection start point) to the ending (the detection end point) is 100%. The starting of the position data of the axis to be inspected is 0% and the ending thereof is 100%. For example, the inspection-process start point and the inspection-process end point can be designated on the basis of the following command described in the robot program.

FsTBat, 70, 100

Here, "FsTBat" is a robot language (a command) for designating the inspection-process start point and the inspection-process end point by the ratio to the total travel distance; and "70, 100" means that a position of 70% is designated as the inspection-process start point and a position of 100% is designated as the inspection-process end point.

The cutout unit 11 cuts out a waveform in the range designated by the inspection-range designation unit 10 out of the force waveform detected by the force acquisition unit 3 and the position acquisition unit 5 and sends the cut out waveform to the inspection unit 8. Because the cutout unit 11 excludes information needless to measure the characteristics from the detected force waveform, the time required for the inspection process can be reduced.

The inspection unit 8 measures the characteristics of the elastic component on the basis of the force waveform cut out by the cutout unit 11 and the inspection parameter designated by the inspection-parameter designation unit 9. The axis to be inspected by the inspection unit 8 is designated by the inspection-unit number selection unit 7. Further, the inspecting operation to be performed by the inspection unit 8 is different for each inspection unit number. For example, the inspecting operation for calculating the modulus of elasticity (a spring constant when the elastic component is a spring) as the characteristics is described later.

The inspection unit 8 includes a reference-characteristics calculation unit 81, a characteristic-change-point recognition unit 82, and a characteristics calculation unit 83. The reference-characteristics calculation unit 81 calculates reference characteristics (described later) from the cut out force waveform. The characteristic-change-point recognition unit 82 specifies a physical characteristic change point on the basis of the calculated reference characteristics, and specifies a section between two physical characteristic change points. Hereinafter, the section between two physical characteristic change points may be referred to as "characteristic section". The characteristics calculation unit 83 calculates the characteristics on the basis of the force waveform of the characteristic section. The characteristics calculation unit 83 sends the calculated characteristics to the inspection output unit 12 and the display unit 13. The characteristics calculation unit 83 can send the characteristic section or the physical characteristic change point together with the characteristics to the inspection output unit 12 and the display unit 13.

The inspection output unit 12 can notify the information sent from the inspection unit 8 to an external control device via I/O or the like. The external control device can use the notified information to execute production control. Specifically, the external control device confirms whether the modulus of elasticity of the elastic component is within a rated range, and if the modulus of elasticity is not within the rated range, the external control device can determine that the product is defective. Further, for example, when the inspecting operation is performed immediately after the workpiece has been assembled, the external control device can confirm whether the assembly work is successfully done by comparing force detection values at a point of the start and at an end point of the characteristic section or the position detection value, or both values with the force detection values at the point of the start and the end point or the position detection value, or both values when the assembly work has been normally complete.

The display unit 13 is a display such as an LCD. The display unit 13 can be a programmable display device that processes input information according to a predetermined program and displays the processed information. The display unit 13 displays the force waveform detected by the force acquisition unit 3 and the position acquisition unit 5 in a graph, or displays the information that is input from the inspection unit 8.

Any of or all of the storage unit 1, the inspection-unit number selection unit 7, the inspection-parameter designation unit 9, the inspection-range designation unit 10, the cutout unit 11, the inspection unit 8, the inspection output unit 12, and the display unit 13 can be realized by a computer having a storage device, an arithmetic device, an input device, and a display device. For example, the storage device is configured by a ROM or a RAM, or a combination thereof, and stores therein the inspection program in advance. The storage device functions as the storage unit 1. The arithmetic device functions as any of or all of the storage unit 1, the inspection-unit number selection unit 7, the inspection-parameter designation unit 9, the inspection-range designation unit 10, the cutout unit 11, the inspection unit 8, and the inspection output unit 12, by executing the inspection program stored in the storage device. The input device is, for example, a mouse and a keyboard, and sends input information from an operator to the arithmetic device. The display device is, for example, a display such as an LCD, and functions as the display unit 13. The computer can be incorporated in a robot controller that controls the robot 2.

Figure 3:
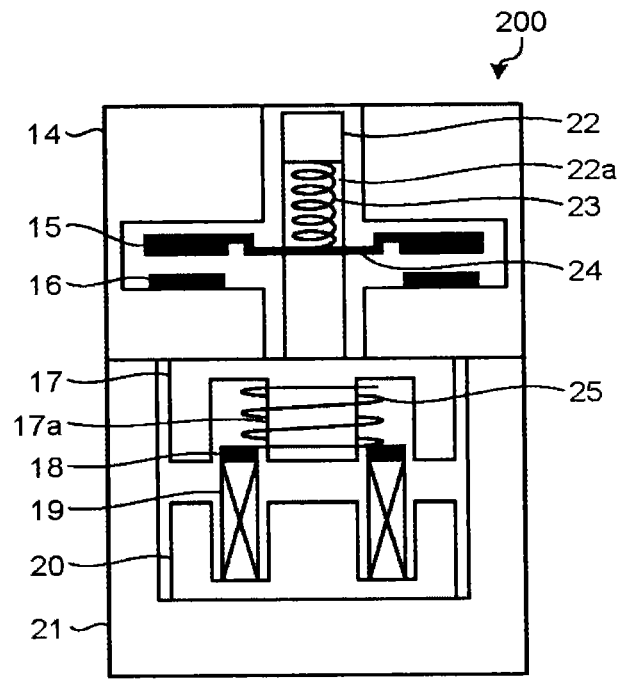
FIG. 3 is a diagram illustrating a mechanism of an electromagnetic contactor as an example of an inspection object.

An inspection object for the inspecting device 100 according to the embodiment of the present invention is described next. FIG. 3 is a diagram illustrating a mechanism of an electromagnetic contactor as an example of the inspection object.

An electromagnetic contactor 200 includes a housing upper part 14, a movable contact point 15, a fixed contact point 16, a movable iron core 17, a plate 18, a magnetizing coil 19, a fixed iron core 20, a housing lower part 21, a push bar 22, a contact spring 23, a movable contact 24, and a tripping spring 25. The movable iron core 17 includes a movable iron-core central part 17a. The push bar 22 includes a window 22a. FIG. 3 illustrates a mechanism of the electromagnetic contactor 200 in a state where the magnetizing coil 19 is not magnetized.

The housing upper part 14 and the housing lower part 21 are fixed by a fixing component (for example, a screw). The magnetizing coil 19 is disposed inside of the housing lower part 21. The magnetizing coil 19 is held inside of the fixed iron core 20. The plate 18 is attached to an upper part of the magnetizing coil 19. The movable iron core 17 is disposed so as to face the fixed iron core 20 with a predetermined gap from the fixed iron core 20. The tripping spring 25 is provided between the fixed iron core 20 and the movable iron core 17. The tripping spring 25 is disposed so as to be wound around the movable iron-core central part 17a. The tripping spring 25 is sandwiched between the plate 18 and the movable iron core 17. The tripping spring 25 is in a compressed state at any time so as to generate a force in an extending direction. The push bar 22 is provided on an upper part of the movable iron core 17. The push bar 22 and the movable iron core 17 are fixed together. The push bar 22 and the movable iron core 17 are guided by the housing upper part 14 and the housing lower part 21 so as to be able to slide in a vertical direction integrally. A hole is bored in the housing upper part 14, and the hand 4 is inserted from the hole, thereby enabling the push bar 22 to move downward (that is, in a direction further compressing the tripping spring 25).

The window 22a is provided in the middle of the push bar 22. The movable contact 24 is held in the window 22a. The movable contact 24 is biased downward by the contact spring 23 formed of a compression coil spring so as to be able to slide along the window 22a. The movable contact point 15 is attached respectively to the opposite ends of the movable contact 24. Further, the movable contact point 15 is disposed so as to face the fixed contact point 16 with a predetermined gap therebetween. The fixed contact point 16 is attached to a part of the housing upper part 14.

Figure 4:
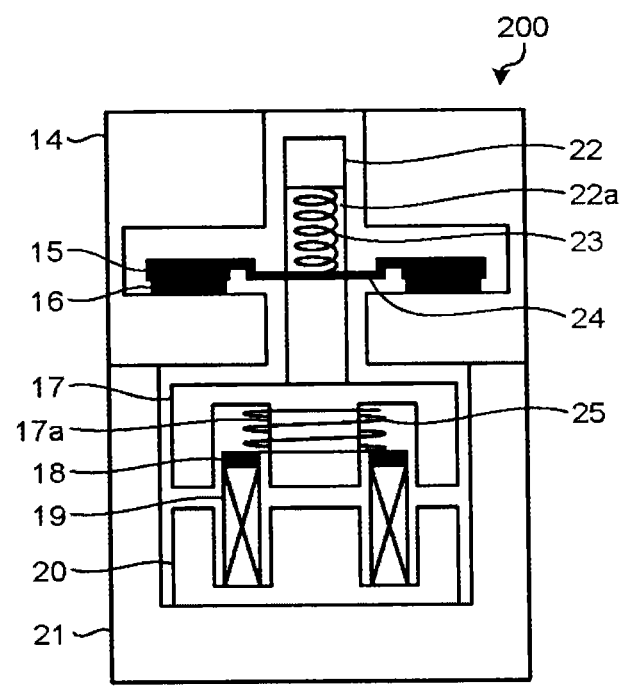
FIG. 4 is a diagram illustrating a mechanism of an electromagnetic contactor when a voltage is applied to a magnetizing coil.
Figure 5:
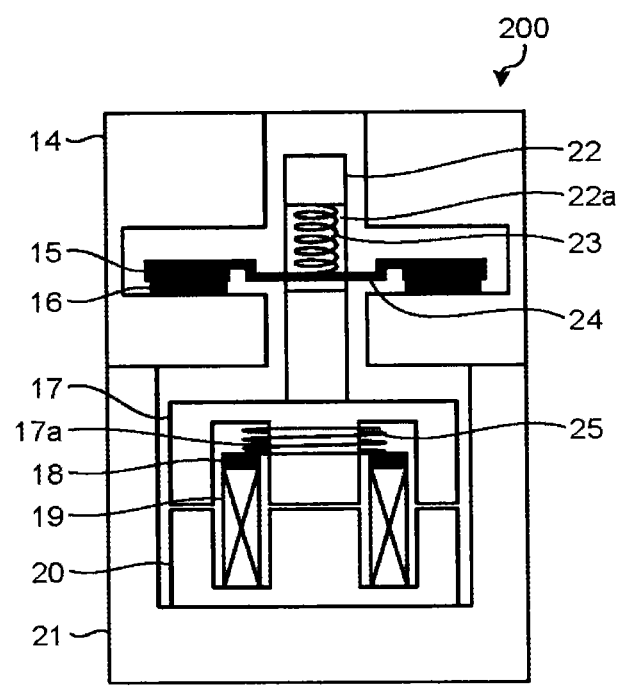
FIG. 5 is a diagram illustrating a mechanism of the electromagnetic contactor when a voltage is applied to the magnetizing coil.
Figure 6:
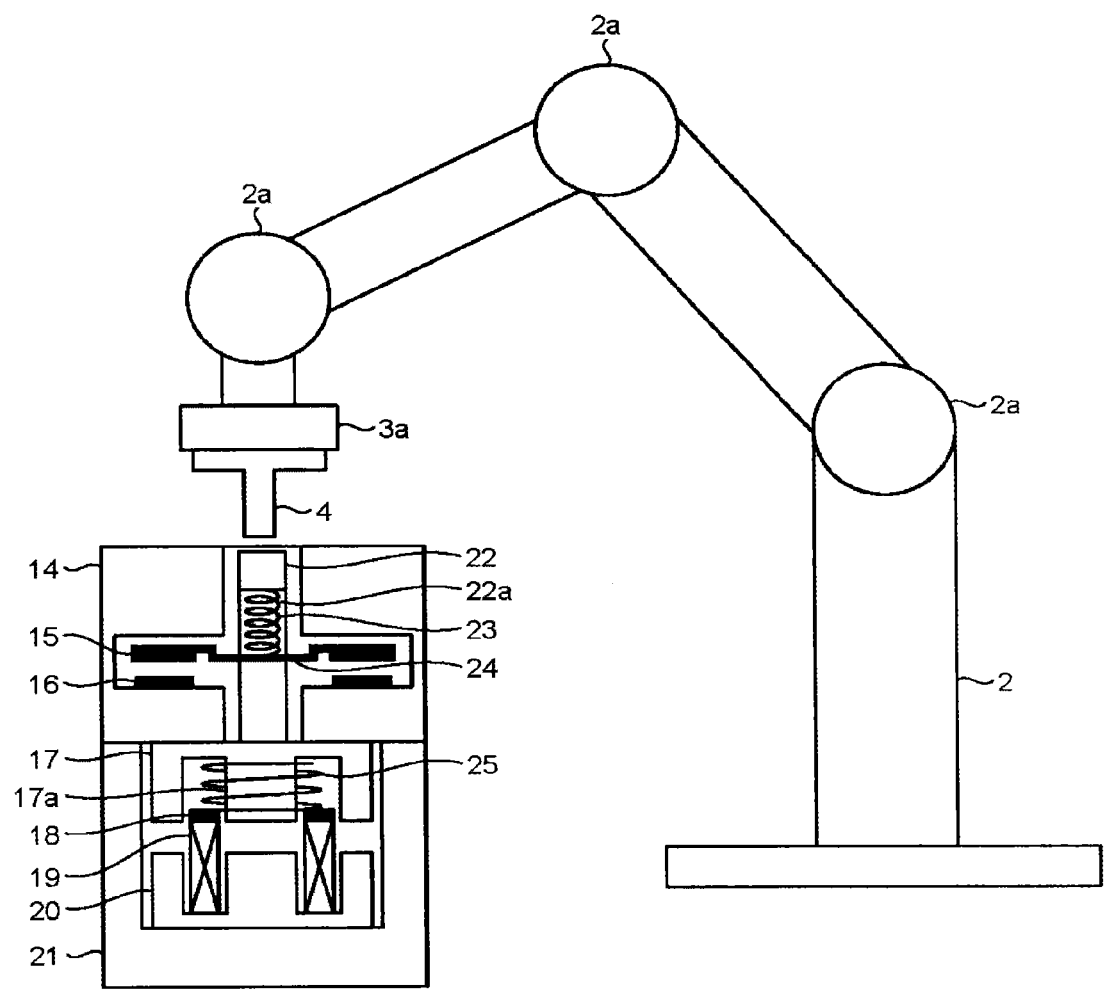
FIG. 6 is a diagram illustrating an operation of the robot.

FIGS. 4 and 5 are explanatory diagrams of a mechanism of the electromagnetic contactor 200 when a voltage is applied to the magnetizing coil 19. When a voltage is applied to the magnetizing coil 19, electric current flows to the magnetizing coil 19; and the magnetizing coil 19 generates magnetic flux. A force of attraction due to the magnetic flux generated by the magnetizing coil 19 is generated between the fixed iron core 20 and the movable iron core 17. When the force of attraction exceeds the biasing force by the tripping spring 25, the movable iron core 17 and the push bar 22 move downward so as to compress the tripping spring 25. Because the movable iron core 17 is attached to the push bar 22, the movable contact point 15 and the fixed contact point 16 come into contact with each other due to the movement of the push bar 22. FIG. 4 is a diagram illustrating a mechanism of the electromagnetic contactor 200 in a state at the moment when the movable contact point 15 and the fixed contact point 16 come into contact with each other.

FIG. 5 is a diagram illustrating a mechanism of the electromagnetic contactor 200 in a state where a stronger voltage is further applied to the movable contact point 15 and the fixed contact point 16 being into contact with each other. The gap between the movable iron core 17 and the fixed iron core 20 is set to be larger than the gap between the movable contact point 15 and the fixed contact point 16. Therefore, if a stronger voltage is applied in a state where the movable contact point 15 and the fixed contact point 16 are brought into contact with each other, the push bar 22 moves further downward in the state where the movable contact point 15 and the fixed contact point 16 being into contact with each other. With this configuration, compression of the contact spring 23 is started, and the tripping spring 25 is further compressed. The biasing force of the contact spring 23 to the movable contact 24 becomes contact pressure between the movable contact point 15 and the fixed contact point 16.

Because the movable contact point 15 and the fixed contact point 16 come into contact with each other, a closing operation of the electromagnetic contactor 200 is complete. That is, an external electric circuit is connected thereto. When the voltage application to the magnetizing coil 19 is stopped, the force of attraction between the movable iron core 17 and the fixed iron core 20 disappears. Consequently, the movable iron core 17 and the push bar 22 move upward in FIG. 5 due to the biasing force of the tripping spring 25; and the movable contact point 15 and the fixed contact point 16 are separated from each other. In this way, an opening operation is complete. That is, the external electric circuit is disconnected.

The contact pressure between the movable contact point 15 and the fixed contact point 16 needs to be maintained properly. If the contact force is not sufficient when the movable contact point 15 and the fixed contact point 16 make contact with each other, the contact state between the movable contact point 15 and the fixed contact point 16 becomes unstable. The unstable contact state causes loose connection. On the other hand, if the contact force is too high when the movable contact point 15 makes contact with the fixed contact point 16, the movable contact point 15 or the fixed contact point 16 causes deformation due to the pressure, thereby reducing the service life of the movable contact point 15 or the fixed contact point 16. In order to apply an appropriate contact force between the movable contact point 15 and the fixed contact point 16, the force of attraction needs to be controlled between the movable contact point 15 and the fixed contact point 16 due to the voltage applied to the magnetizing coil 19 and the spring force of the tripping spring 25.

An operation of the inspecting device 100 according to the first embodiment of the present invention is described next.

FIGS. 6 to 10 are explanatory diagrams of an operation of the robot 2. The robot 2 is driven under the control of the robot program. In the inspecting operation, the robot 2 pushes down the push bar 22 of the electromagnetic contactor 200 by using the end of the hand 4. That is, the robot 2 pushes the push bar 22 in a compression direction of the tripping spring 25, among the directions of action of the tripping spring 25.

Figure 7:
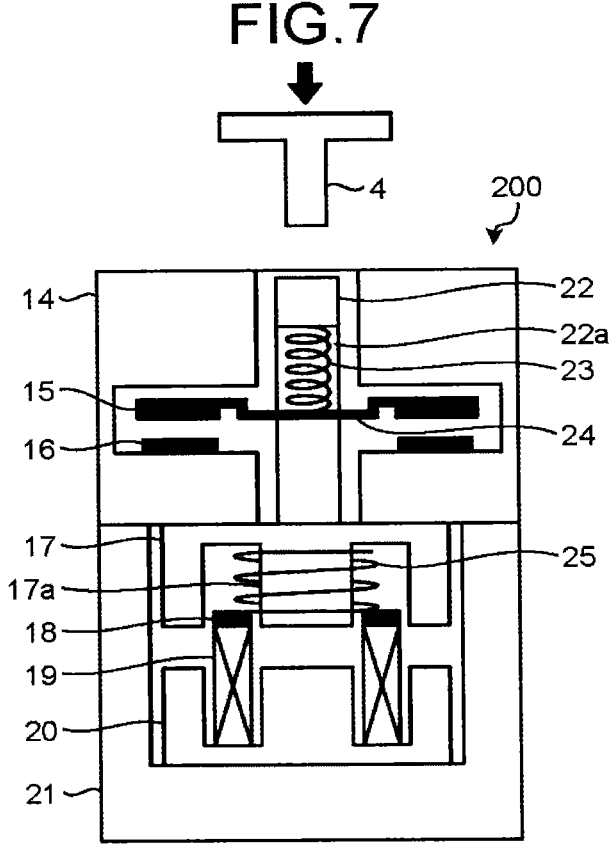
FIG. 7 is a diagram illustrating an operation of the robot.
Figure 8:
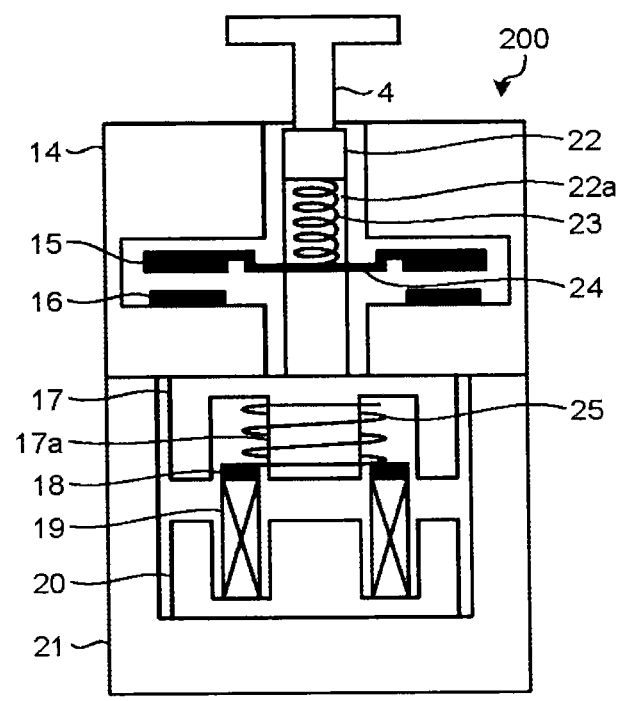
FIG. 8 is a diagram illustrating an operation of the robot.
Figure 9:
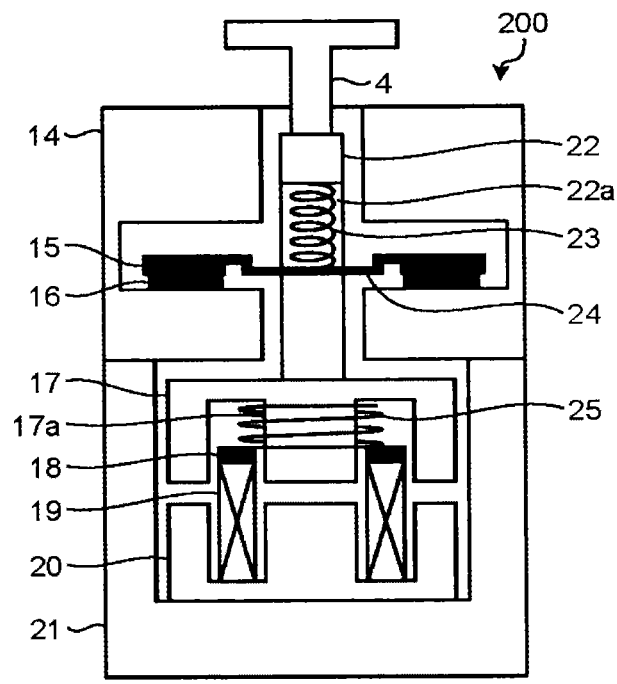
FIG. 9 is a diagram illustrating an operation of the robot.
Figure 10:
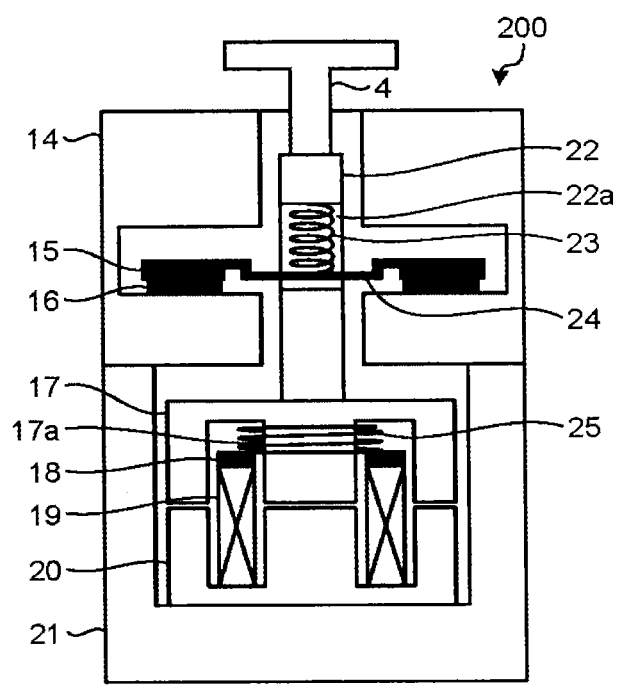
FIG. 10 is a diagram illustrating an operation of the robot.

The positional relation between the hand 4 and the electromagnetic contactor 200 in a period from the start of the movement of the hand 4 in the direction of the arrow by the robot 2 until the end of the movement is illustrated in FIGS. 7 to 10. FIG. 7 is a diagram illustrating a position relation between the hand 4 and the electromagnetic contactor 200 in a state immediately before the inspecting operation (a state 1). FIG. 8 is a diagram illustrating the position relation between the hand 4 and the electromagnetic contactor 200 in a state when the contact just occurs between the hand 4 and the push bar 22 (a state 2). FIG. 9 is a diagram illustrating the position relation between the hand 4 and the electromagnetic contactor 200 at the moment of contact between the movable contact point 15 and the fixed contact point 16 (a state 3). FIG. 10 is a diagram illustrating the position relation between the hand 4 and the electromagnetic contactor 200 in a state where the inspecting operation is finished (a state 4).

Figure 11:
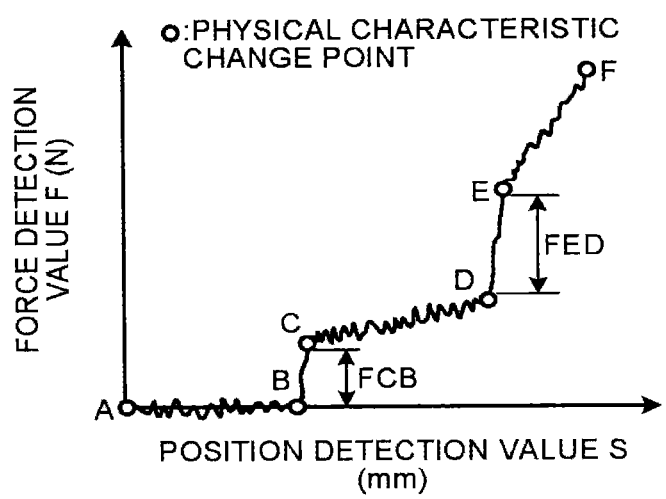
FIG. 11 is a diagram illustrating an example of a force waveform.

FIG. 11 is a diagram illustrating an example of a force waveform acquired by the force acquisition unit 3 and the position acquisition unit 5, when operations are sequentially performed from the state of the position relation between the hand 4 and the electromagnetic contactor 200 illustrated in FIG. 7 to the state thereof illustrated in FIG. 10. A force detection value F (the unit is N) is plotted on a horizontal axis and a position detection value S (the unit is millimeters) is plotted on a vertical axis, in the force waveform.

In FIG. 11, a section from point A to point B corresponds to a state before the hand 4 comes into contact with the push bar 22 (that is, the state 1). The point B corresponds to the state 2. A section front point C to point D corresponds to a state before the movable contact point 15 and the fixed contact point 16 come into contact with each other, and corresponds to a compressed state of the tripping spring 25. The point D corresponds to the state 3. A section from point E to point F corresponds to a state after the movable contact point 15 and the fixed contact point 16 come into contact with each other; and a state where the contact spring 23 and the tripping spring 25 are simultaneously compressed. The point F corresponds to the state 4.

A difference FCB between the force detection value at the point B and the force detection value at the point C corresponds to the force generated by the tripping spring 25 (the biasing force of the tripping spring 25), when a voltage is not applied to the magnetizing coil 19. A difference FED between the force detection value at the point D and the force detection value at the point E corresponds to the force generated by the contact spring 23 (the biasing force by the contact spring 23), when a voltage is not applied to the magnetizing coil 19.

As illustrated in FIG. 11, the point C and the point D need to be specified in order to acquire the spring constant of the tripping spring 25. The point B and the point C also need to be specified in order to acquire the biasing force of the tripping spring 25. Note that measurement noise components are added both to the detection values by the force acquisition unit 3 and the position acquisition unit 5, the force waveform becomes a sawtooth waveform.

An operation is described next in which the inspecting device 100 calculates characteristics. An operation is described here to detect a characteristic that is the spring force of the tripping spring 25 in the electromagnetic contactor 200.

An operation in which the robot 2 moves a hand from the state 1 to the state 4 is performed on the basis of the robot program. During the operation, the inspecting device 100 acquires the force waveform from the detection start point to the detection end point set by the acquired-condition designation unit 6. The cutout unit 11 cuts out a force waveform in a range designated by the inspection-range designation unit 10 (hereinafter, "partial waveform") from the acquired force waveform and sends the cut out partial waveform to the inspection unit 8.

Figure 12:
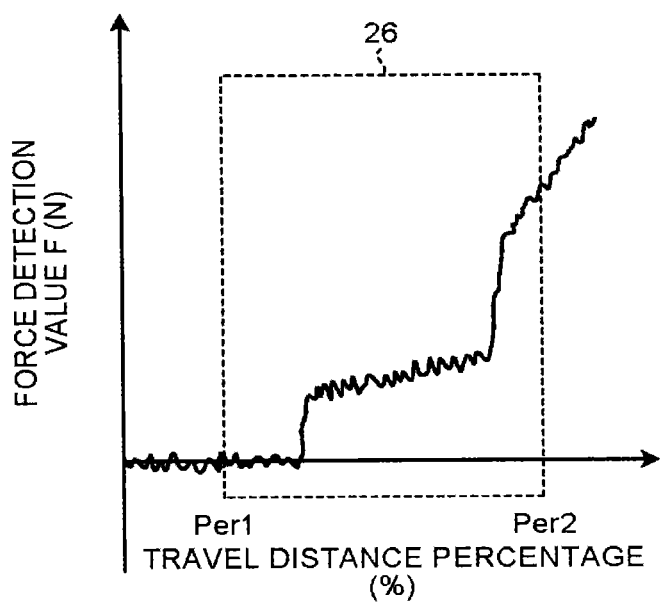
FIG. 12 is a diagram illustrating a partial waveform.

FIG. 12 is a diagram illustrating a partial waveform. The force detection value F is plotted on a horizontal axis; and the ratio of a travel distance, which is compared with the total travel distance from the detection start point to the detection end point assumed to be 100% (hereinafter, the percentage is referred to as "travel distance percentage"), is plotted on a vertical axis respectively in a graph of FIG. 12.

A pair of the force detection value F and the position detection value S detected by the force acquisition unit 3 and the position acquisition unit 5 is discrete data collected in the set sampling period. When the number of pieces of data is assumed to be n, the travel distance percentage related to the i-th data is calculated according to the following mathematical expression 1.

$$\text{Per}(i) = \{S(i)/S(n)\} * 100 \quad (i=1,2,\ldots,n) \tag{1}$$

In the example illustrated in FIG. 12, the force waveform in a range from Per1 to Per2 is cut out as the partial waveform (the partial waveform 26).

Subsequently, the inspection-unit number selection unit 7 selects an inspection unit number "53" indicating an inspecting operation of calculating the spring force. The inspection unit 8 performs the inspecting operation corresponding to the inspection unit number "53".

Figure 13:
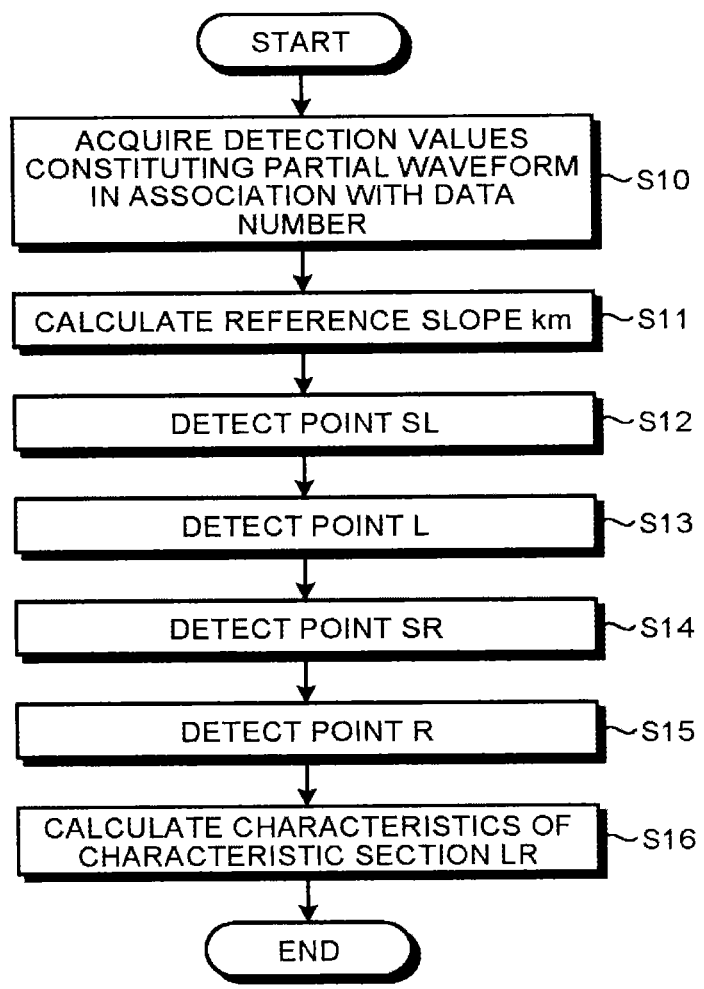
FIG. 13 is a flowchart illustrating an outline of an inspecting operation.
Figure 14:
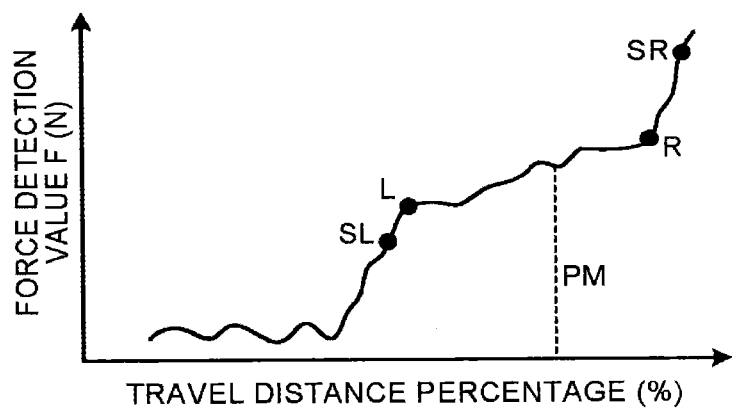
FIG. 14 is a diagram illustrating various values related to the inspecting operation.

FIG. 13 is a flowchart illustrating an outline of an inspecting operation performed by the inspection unit 8; and FIG. 14 is a diagram illustrating various values related to the inspecting operation by the inspection unit 8.

In FIG. 14, a horizontal axis indicates the force detection value F, and a vertical axis indicates a travel distance percentage. A section from a point L to a point R is a characteristic section (a characteristic section LR) of the tripping spring 25. The point L is a physical characteristic change point at a point of starting of the characteristic section LR, and the point R is a physical characteristic change point at the end of the characteristic section LR. The point L corresponds to a deformation start point of the tripping spring 25 (that is, a point that the movable iron core 17 is just separated from the housing upper part 14); and the point R corresponds to a point where the state 3 has been reached (a deformation end point of the tripping spring 25 alone, that is, a point before the tripping spring 25 is compressed together with the contact spring 23). A point PM is an intermediate point of the characteristic section LR, and is an inspection parameter that can be set when the inspection unit number "53" is selected. In other words, the point PM is an arbitrary designated point of the force waveform in the process of deformation of the elastic component. As the point PM, a rough position in the middle of the force detection value from the deformation start point to the deformation end point of the tripping spring 25, which is the elastic component to be inspected, can be set by using a travel distance percentage. A point SL is an adjacent point to the point L, and a point SR is an adjacent point to the point R. The point SL is a point having a smaller travel distance than the point L, and the point SR is a point having a larger travel distance than the point R.

As illustrated in FIG. 13, the reference-characteristics calculation unit 81 first acquires the pair of the force detection value F and the position detection value S in the inspection range constituting the partial waveform 26 in association with the data number (Step S10). The reference-characteristics calculation unit 81 then calculates a slope (km) at the point PM (Step S11). The reference-characteristics calculation unit 81 sends the calculated slope km as a reference characteristic (hereinafter, also "reference slope") to the characteristic-change-point recognition unit 82.

Subsequently, the characteristic-change-point recognition unit 82 specifies the point SL as a rough change point (Step S12); and specifies the point L based the specified point SL (Step S13). The characteristic-change-point recognition unit 82 then specifies the point SR as a rough change point (Step S14); and specifies the point R on the basis of the specified point SR (Step S15). The characteristic-change-point recognition unit 82 sends the data number of the point L and the data number of the point R to the characteristics calculation unit 83.

Subsequently, the characteristics calculation unit 83 calculates characteristics on the basis of the data of the characteristic section LR of the partial waveform (Step S16). In this process, the characteristics calculation unit 83 calculates, for example, a mean value of the spring force in the characteristic section LR. The characteristics calculation unit 83 sends the calculated characteristic to the inspection output unit 12 and the display unit 13. After the process at Step S16, the operation of the inspection unit is finished.

For example, the spring force can be obtained by the following procedure. First, the point C and the point D in FIG. 11 are specified by the above operation. Further, because an arbitrary point in the section from the point A to the point B is designated, the point B is specified by an operation identical to the above operation. It is because the section from the point A to the point B can be regarded as the process of deformation in which the modulus of elasticity is 0; and the point B can be regarded as a deformation end point of the process of deformation. By specifying the point B and the point C, the biasing force FCB of the tripping spring 25 is obtained. Further, by specifying the point C and the point D, the spring constant as the modulus of elasticity of the tripping spring 25 is obtained. An arbitrary spring force from the point C to the point D is obtained on the basis of the point C, the biasing force FCB, and the spring constant of the tripping spring 25.

Respective processes at Step S11 to Step S13 are described next in more detail.

It is assumed that the inspection parameter designated by the inspection-parameter designation unit 9 includes a left slope scaling factor SlpL, a right slope scaling factor SlpR, and an approximate window distance d, in addition to the designation of the point PM. In the example, the left slope scaling factor SlpL (first parameter) and the right slope scaling factor SlpR (first parameter) are both larger than 1.

First, at Step S11, the reference-characteristics calculation unit 81 searches for data having a travel distance percentage that is closest to the point PM. The data number of data having the travel distance percentage closest to the point PM is designated as Mn.

Figure 15:
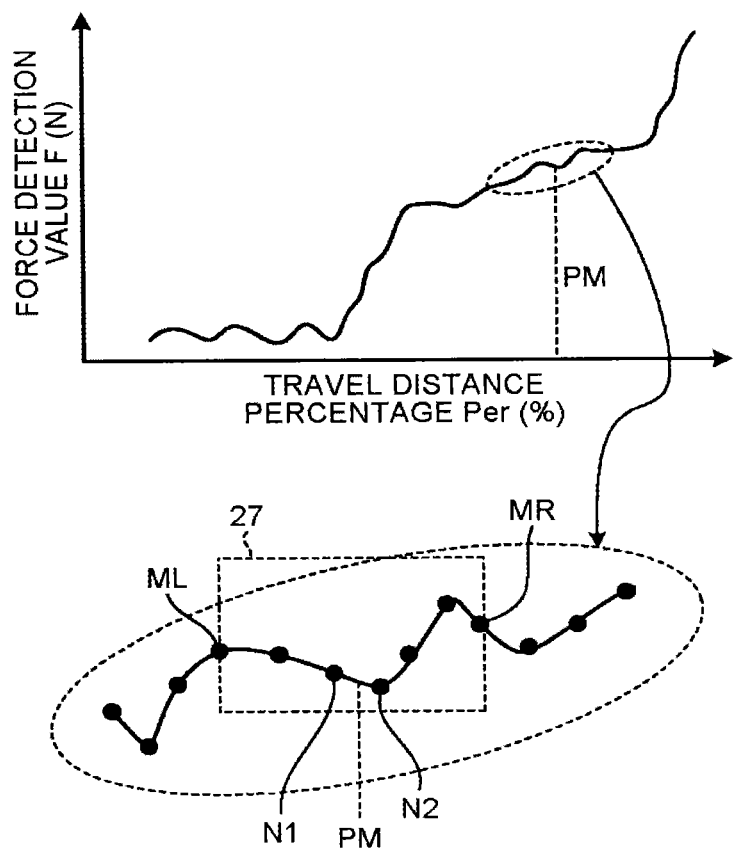
FIG. 15 is a diagram illustrating a process at Step S11.

FIG. 15 is a diagram illustrating a process at Step S11. The data of the data number Mn is searched in the following manner. That is, the reference-characteristics calculation unit 81 first obtains data having a travel distance percentage smaller than the point PM and the largest data number (the data number of the data is designated as N1). The reference-characteristics calculation unit 81 calculates the data number N1 by using the following mathematical expressions (2) to (3). The travel percentage of the point PM is denoted as "PM".

$$\text{Per}(i) \leq PM (i=1,2,\ldots,n) \tag{2}$$

$$N1 = \max(i) \tag{3}$$

Note that there are relations of Per(1)=0% and Per(n)=100%.

Next, the reference-characteristics calculation unit 81 obtains data having a travel distance percentage larger than the point PM and the smallest data number (the data number of this data is referred to be N2). The reference-characteristics calculation unit 81 calculates the data number N2 by using the following mathematical expression (4).

$$N2 = N1+1 \tag{4}$$

The reference-characteristics calculation unit 81 then assumes Mn=N1 when the following mathematical expression (5) is satisfied, and assumes Mn=N2 when the following mathematical expression (5) is not satisfied.

$$\text{Per}(N2)-PM > PM-\text{Per}(N1) \tag{5}$$

After the data having the data number Mn is specified, the reference-characteristics calculation unit 81 searches for data having the smallest data number ML and data having the largest data number MR, among data included in a window 27 in which the size of the range of the travel distance percentage corresponds to the approximate window distance d, setting the data having the data number Mn as the center. Specifically, the reference-characteristics calculation unit 81 obtains the data number ML by using the following mathematical expressions (6) to (7).

$$S(Mn)-S(i) \geq d/2 (i=Mn-1, Mn-2, \ldots, 1) \quad (6)$$

$$ML = \min(i) \quad (7)$$

The reference-characteristics calculation unit 81 also obtains the data number MR by using the following mathematical expressions (8) and (9).

$$S(i)-S(Mn) \geq d/2 (i=Mn+1, Mn+2, \ldots, n) \quad (8)$$

$$MR = \max(i) \quad (9)$$

Subsequently, the reference-characteristics calculation unit 81 calculates a slope of an approximate line of all the pieces of data included in the window 27, and designates the calculated slope as a reference slope km. The reference-characteristics calculation unit 81 can calculate the reference slope km by using a least-square method for all the pieces of data included in the window 27.

Figure 16:
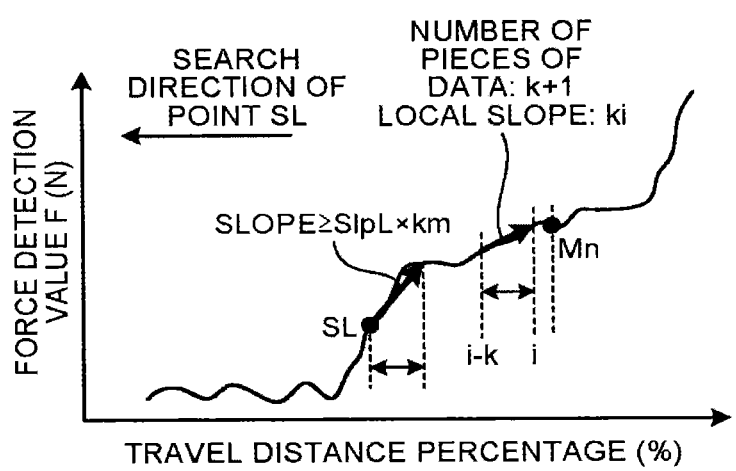
FIG. 16 is a diagram illustrating a process at Step S12 in the first embodiment.
Figure 17:
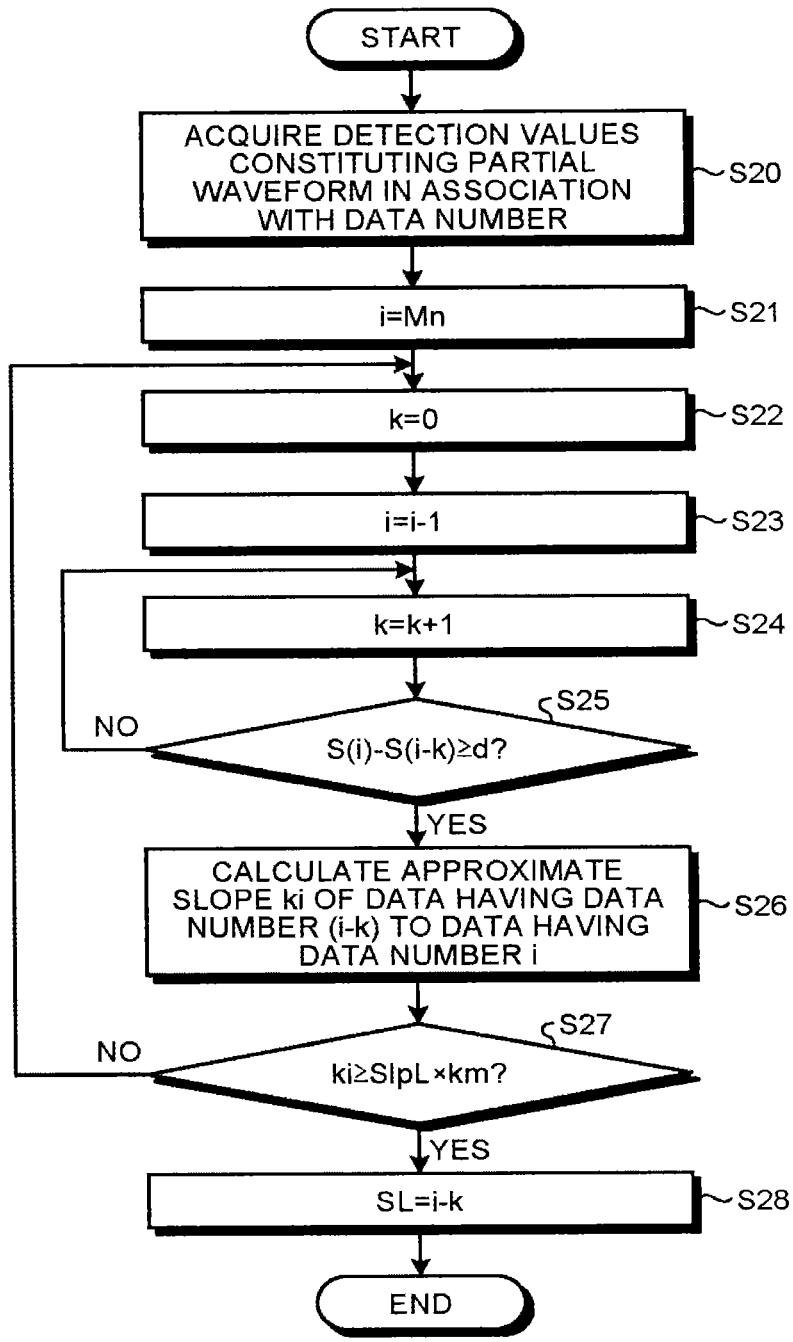
FIG. 17 is a flowchart illustrating a detailed operation of the process at Step S12 in the first embodiment.

FIG. 16 is a diagram illustrating a process at Step S12; and FIG. 17 is a flowchart illustrating a detailed operation of the process at Step S12. In the process at Step S12, the characteristic-change-point recognition unit 82 executes searches of the point SL in a negative direction (or to be described more accurately as being in a negative direction using the point PM as the point of the starting).

The characteristic-change-point recognition unit 82 first acquires the pair of the force detection value F and the position detection value S in the inspection range constituting the partial waveform 26 in association with the data number (Step S20). The characteristic-change-point recognition unit 82 then initializes a variable i by Mn (Step S21), and initializes a variable k by 0 (Step S22).

Subsequently, the characteristic-change-point recognition unit 82 decrements the variable i by 1 (Step S23) and increments the variable k by 1 (Step S24). The characteristic-change-point recognition unit 82 then determines whether the following mathematical expression (10) is satisfied (Step S25).

$$S(i)-S(i-k) \geq d \quad (10)$$

If the mathematical expression (10) is not satisfied (NO at Step S25), the characteristic-change-point recognition unit 82 performs the process at Step S24 again. If the mathematical expression (10) is satisfied (YES at Step S25), the characteristic-change-point recognition unit 82 calculates the slope of the approximate line from data having the data number i−k to data having the data number i (Step S26). The characteristic-change-point recognition unit 82 sets the calculated slope as a local slope ki. The characteristic-change-point recognition unit 82 can calculate the local slope ki by using the least-square method for the pieces of data having the data number from i−k to i.

Subsequently, the characteristic-change-point recognition unit 82 uses the reference slope km, the left slope scaling factor SlpL, and the calculated local slope ki so as to determine whether the following mathematical expression (11) is satisfied (Step S27).

$$ki \geq SlpL*km \quad (11)$$

If the mathematical expression (11) is not satisfied (NO at Step S27), the characteristic-change-point recognition unit 82 performs the process at Step S22 again. If the mathematical expression (11) is satisfied (YES at Step S27), the characteristic-change-point recognition unit 82 designates SL as i−k (Step S28) and finishes the process at Step S12.

Figure 18:
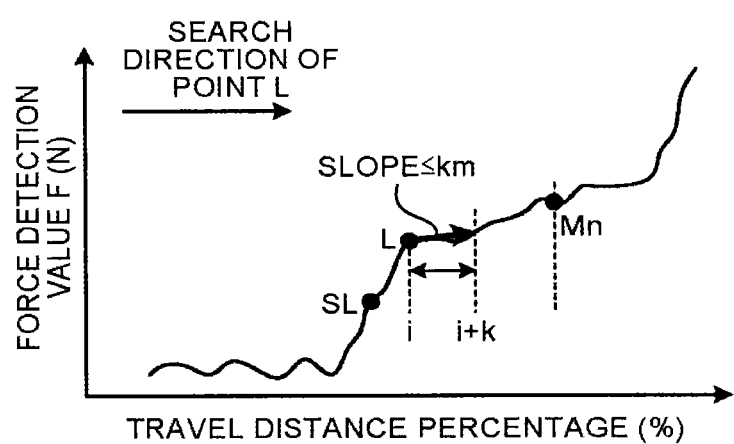
FIG. 18 is a diagram illustrating a process at Step S13.
Figure 19:
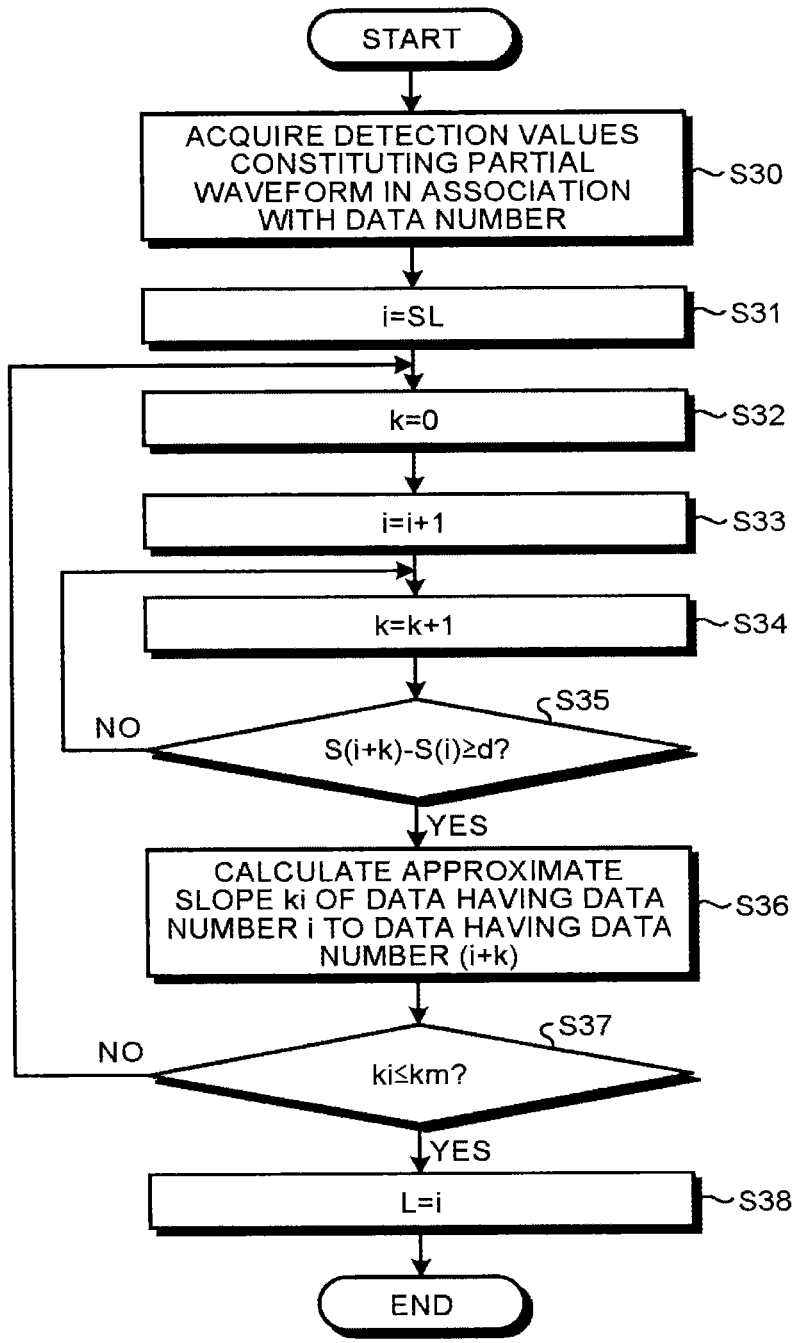
FIG. 19 is a flowchart illustrating a detailed operation of the process at Step S13.

FIG. 18 is a diagram illustrating a process at Step S13; and FIG. 19 is a flowchart illustrating a detailed operation of the process at Step S13. In the process at Step S13, the characteristic-change-point recognition unit 82 searches for the point L in a positive direction using the point SL as the point of the starting.

The characteristic-change-point recognition unit 82 first acquires the pair of the force detection value F and the position detection value S in the inspection range constituting the partial waveform 26 in association with the data number (Step S30). The characteristic-change-point recognition unit 82 initializes the variable i by SL (Step S31) and initializes the variable k by 0 (Step S32).

Subsequently, the characteristic-change-point recognition unit 82 increments the variable i by 1 (Step S33) and increments the variable k by 1 (Step S34). The characteristic-change-point recognition unit 82 then determines whether the following mathematical expression (12) is satisfied (Step S35).

$$S(i+k)-S(i) \geq d \quad (12)$$

If the mathematical expression (12) is not satisfied (NO at Step S35), the characteristic-change-point recognition unit 82 performs the process at Step S34 again. If the mathematical expression (12) is satisfied (YES at Step S35), the characteristic-change-point recognition unit 82 calculates the slope of the approximate line plotted from data having the data number of i to data having the data number i+k (Step S36). The characteristic-change-point recognition unit 82 designates the calculated slope as the local slope ki. The characteristic-change-point recognition unit 82 can calculate the local slope ki by using the least-square method for the pieces of data having the data number from i to i+k.

Subsequently, the characteristic-change-point recognition unit 82 uses the reference slope km and the calculated local slope ki so as to determine whether the following mathematical expression (13) is satisfied (Step S37).

$$ki \leq km \quad (13)$$

If the mathematical expression (13) is not satisfied (NO at Step S37), the characteristic-change-point recognition unit 82 performs the process at Step S32 again. If the mathematical expression (13) is satisfied (YES at Step S37), the characteristic-change-point recognition unit 82 designates L as i (Step S38) so as to finish the process at Step S13.

In this manner, the characteristic-change-point recognition unit 82 calculates the local slope ki at a focus point, which is different from the point PM, thereby determining whether the focus point is the physical characteristic change point on the basis of comparison between the local slope ki at the focus point and the local slope km at the point PM.

More specifically, the characteristic-change-point recognition unit 82 compares the local slope ki at the focus point with a value obtained by multiplying the reference slope km by the left slope scaling factor SlpL, while moving the focus point from the point PM toward the deformation start point; and sets a focus point, at which the local slope ki first reaches the value obtained by multiplying the reference slope km by the left slope scaling factor SlpL, as the point SL. The characteristic-change-point recognition unit 82 compares the local slope ki at the focus point with the reference slope km, while moving the focus point from the point SL toward the point PM, thereby so as to specify a focus point, at which the local slope ki first becomes equal to or smaller than the reference slope km, as the deformation start point.

In other words, the characteristic-change-point recognition unit 82 searches for a focus point that first satisfies such a condition (first condition) that the local slope ki reaches SlpL*km, which is a first threshold on the basis of the reference slope km as a local slope at the point PM and the left slope scaling factor SlpL as "first parameter", while moving the focus point from the point PM toward the deformation start point, thereby specifying the searched focus point as the point SL. The characteristic-change-point recognition unit 82 then searches for a focus point that first satisfies such a condition (second condition) that the local slope ki at the focus point reaches the local slope km at the point PM, while moving the focus point in a direction approaching the point PM from the point SL as the point of the starting, thereby specifying the searched focus point as the point L being the deformation start point.

The characteristic-change-point recognition unit 82 compares the local slope ki at the focus point with a value obtained by multiplying the reference slope km by the right slope scaling factor SlpR, while moving the focus point from the point PM toward the deformation end point; and designates a focus point, at which the local slope ki first reaches the value obtained by multiplying the reference slope km by the right slope scaling factor SlpR, as the point SR. The characteristic-change-point recognition unit 82 compares the local slope ki at the focus point with the reference slope km, while moving the focus point from the point SR toward the point PM, thereby specifying a focus point, at which the local slope ki first becomes equal to or smaller than the reference slope km, as the deformation end point.

That is, the process at Step S14 and the process at Step S15 are respectively identical to the process at Step S12 and the process at Step S13, except in that the search direction of the point SR is opposite to the search direction of the point SL and in that the right slope scaling factor SlpR is used instead of the left slope scaling factor SlpL. Therefore, detailed descriptions of the operations of these processes will be omitted.

As described above, according to the first embodiment of the present invention, the inspecting device 100 includes a force-waveform detection system (the robot 2, the force acquisition unit 3, and the position acquisition unit 5) that applies a load to a workpiece having an elastic component assembled thereto in a direction of action of the elastic component and acquires a force waveform describing a relation between the load and the amount of displacement; the inspection-parameter designation unit 9 as a reception unit that receives an input of an arbitrary designated point (the point PM) in a process of deformation of the elastic component in the force waveform acquired by the force-waveform detection system; and the inspection unit 8 that calculates a local slope of the force waveform at the designated point and specifies the physical characteristic change point including the deformation start point or the deformation end point of the elastic component in the force waveform on the basis of the local slope at the calculated designated point. The inspecting device 100 can specify the physical characteristic change point only by designating the point PM and thus does not require any setting of a comparison reference related to the physical characteristic change point. That is, the inspecting device 100 can specify the deformation start point or the deformation end point of the elastic component much easily. Further, only one point in the process of deformation of the elastic component needs to be designated as the point PM. Therefore, even if the deformation start point or the deformation end point varies for each assembled body due to various errors (including a positioning error of the assembled body or a dimension error of other components disposed around the elastic component), the inspecting device 100 can specify the deformation start point or the deformation end point. Accordingly, because the inspecting operation can be automated, an operator of the inspecting device 100 can avoid the burden of performing various setting for each assembled body.

The inspection-unit number selection unit 7 can display a screen that moves the operator to input the selection of the inspection unit number on the display unit 13 so that the operator performs the input of selection of the inspection unit number. The inspection-parameter designation unit 9 can also display a screen that prompts selection of the inspection parameter on the display unit 13 so that the operator performs an input of selection of the inspection parameter. Further, the acquired-condition designation unit 6 can display a screen that moves the operator to input the sampling period, the detection start point, or the detection end point on the display unit 13 so that the operator performs the input of the sampling period, the detection start point, or the detection end point.

Furthermore, when there are a plurality of identical workpieces and the inspecting operation is performed with respect to the plurality of workpieces, the inspecting device 100 can pick up one of these workpieces as a sample, obtain the force waveform from the detection start point to the detection end point of the sample, and display the obtained force waveform on the display unit 13 and display the screen that prompts an input of the inspection unit number and the inspection parameter. With this configuration, the operator can decide the condition adapted to the characteristics of the plurality of workpieces on the basis of the force waveform of the sample, to input the decided condition.

Second Embodiment

As the configurations of a second embodiment are equivalent to those of the first embodiment, the second embodiment is described while exemplifying constituent elements that are identical to those of the first embodiment and using like reference signs.

In the second embodiment, a force-noise determination value FNoise (third parameter) is given as the inspection parameter. The inspection-parameter designation unit 9 reads a value of the force-noise determination value FNoise from the storage unit 1 and sends the value to the inspection unit 8.

The characteristic-change-point recognition unit 82 compares a difference of loads, which are applied to the pieces of data at the opposite ends of the approximate window distance d, with the value of the force-noise determination value FNoise; and compares the local slope ki at the focus point with the value obtained by multiplying the reference slope km by the left slope scaling factor SlpL, while moving the focus point from the point PM toward the deformation start point. The characteristic-change-point recognition unit 82 designates a focus point, at which the difference becomes equal to or larger than the value of the force-noise determination value FNoise and the local slope ki first reaches the value obtained by multiplying the reference slope km by the left slope scaling factor SlpL, as the point SL.

Furthermore, the characteristic-change-point recognition unit 82 compares the difference of loads, which are applied to the pieces of data at the opposite ends of the approximate window distance d, with the value of the force-noise determination value FNoise; and compares the local slope ki at the focus point with a value obtained by multiplying the reference slope km by the right slope scaling factor SlpR, while moving the focus point from the point PM toward the deformation end point. The characteristic-change-point recognition unit 82 designates a focus point, at which the difference becomes equal to or larger than the value of the force-noise determination value FNoise and the local slope ki first reaches the value obtained by multiplying the reference slope km by the right slope scaling factor SlpR, as the point SR.

Figure 20:
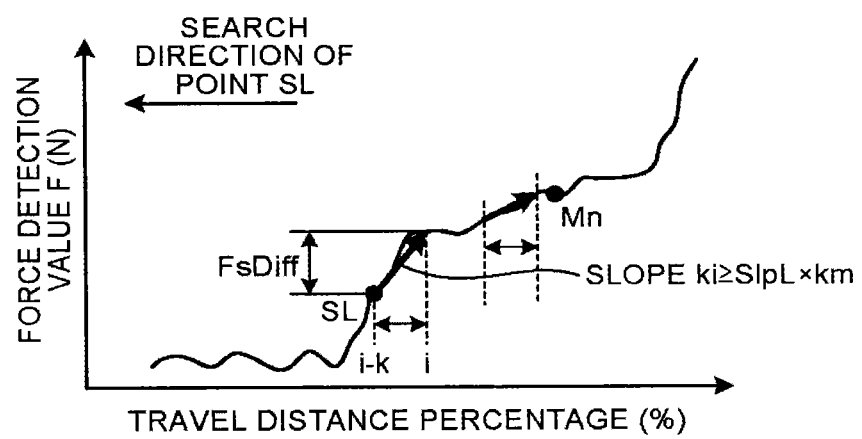
FIG. 20 is a diagram illustrating a process at Step S12 in a second embodiment.
Figure 21:
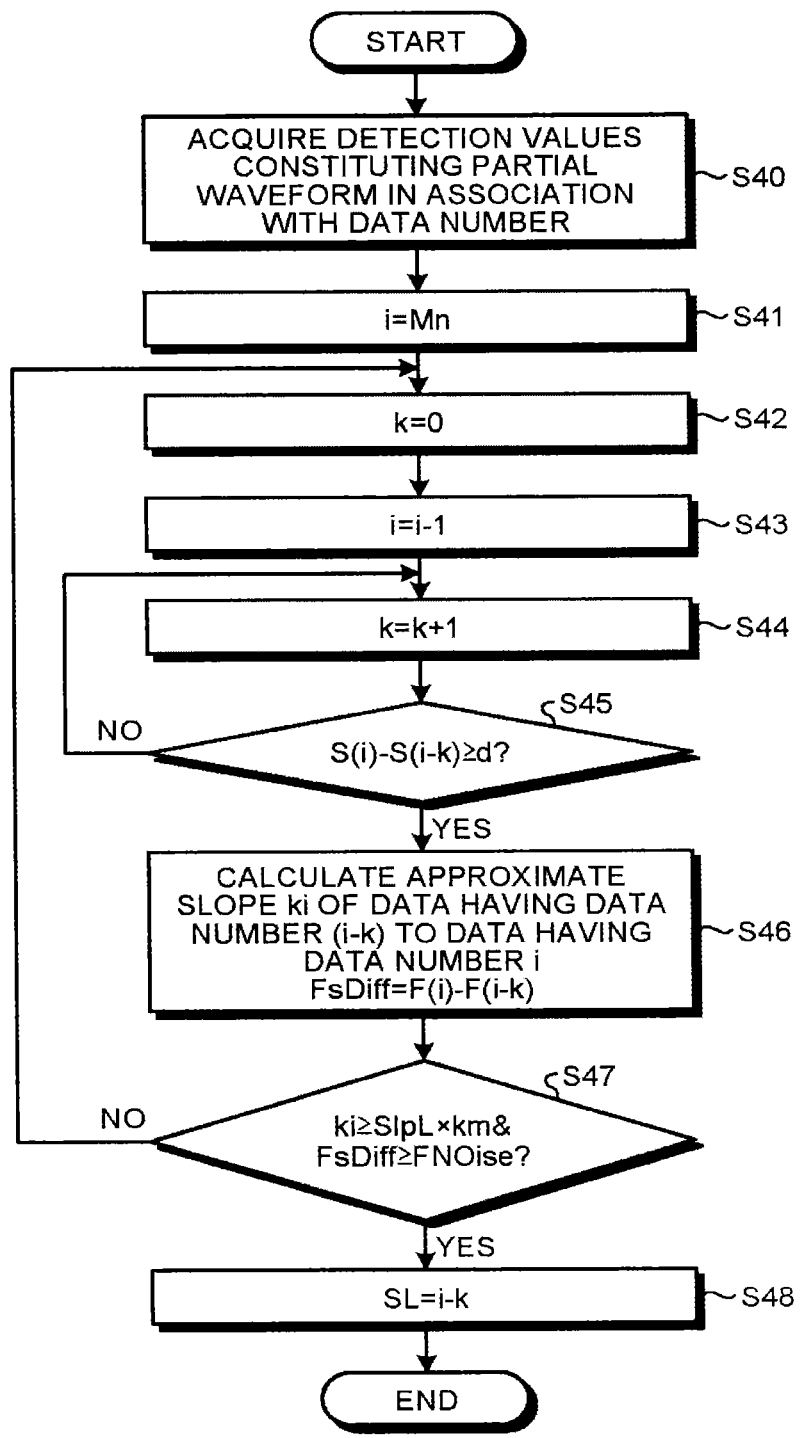
FIG. 21 is a flowchart illustrating a detailed operation of the process at Step S12 in the second embodiment.

FIG. 20 is a diagram illustrating a process at Step S12 in the inspecting device 100 according to the second embodiment; and FIG. 21 is a flowchart illustrating a detailed operation of the process at Step S12 in the inspecting device 100 according to the second embodiment.

Processes at Step S40 to Step S45 are respectively identical to the processes at Step S20 to Step S25, and thus descriptions thereof will be omitted here. In a determination process at Step S45, if the mathematical expression (10) is not satisfied (NO at Step S45), the characteristic-change-point recognition unit 82 performs the process at Step S44 again. If the mathematical expression (10) is satisfied (YES at Step S45), the characteristic-change-point recognition unit 82 calculates the local slope ki and calculates a difference FsDiff by subtracting a force detection value F(i−k) constituting data having a data number i−k from a force detection value F(i) constituting data having a data number i (Step S46).

Subsequently, the characteristic-change-point recognition unit 82 uses the reference slope km, the left slope scaling factor SlpL, the force-noise determination value FNoise, and the calculated local slope ki as well as the difference FsDiff to determine whether both of the following mathematical expressions (14) and (15) are satisfied (Step S47).

$$ki \geq SlpL * km \quad (14)$$

$$FsDiff \geq FNoise \quad (15)$$

If at least one of the mathematical expressions (14) and (15) is not satisfied (NO at Step S47), the characteristic-change-point recognition unit 82 performs the process at Step S42 again. If both of the mathematical expressions (14) and (15) are satisfied (YES at Step S47), the characteristic-change-point recognition unit 82 designates SL as i−k (Step S48) and finishes the process at Step S12.

In this manner, according to the second embodiment, if the force-noise determination value FNoise is designated and a change amount of force at a point away by the approximate window distance d is smaller than the force-noise determination value FNoise, the inspecting device 100 does not specify the point SL. That is, the second condition further includes a condition in which the difference FsDiff of the loads in the data at the opposite ends, which are in the force waveform in the range of the approximate window distance d including the focus point, exceeds the force-noise determination value FNoise as "third parameter". If the change amount of the force decreases due to an influence of noise, the inspecting device 100 may not specify the point SL. Accordingly, the influence of noise can be eliminated when detecting the change point.

Third Embodiment

It is decided whether to set a value of the slope scaling factor (the left slope scaling factor SlpL and the right slope scaling factor SlpR) to be larger than 1 or smaller than 1 on the basis of a search direction and the magnitude of the slope before or after the characteristic change point. When search is started by using the point PM as the point of starting and the slope after the characteristic change point is larger than the slope before the characteristic change point, and if a value larger than 1 is set as the slope scaling factor, the characteristic change point is specified. Further, when the slope after the characteristic change point is smaller than the slope before the characteristic change point, and if a value smaller than 1 is set as the slope scaling factor, the characteristic change point is specified.

Figure 22:
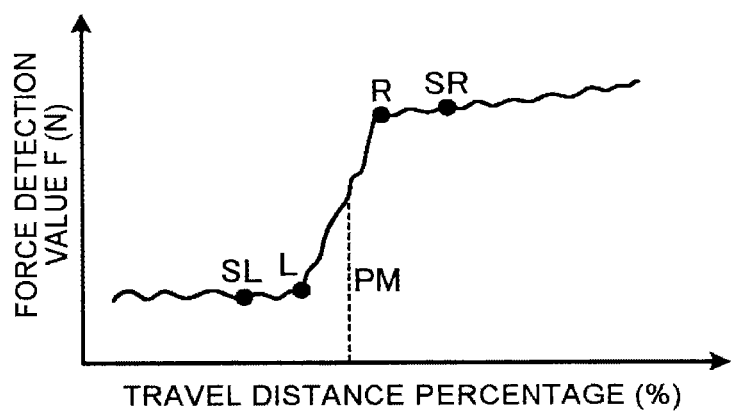
FIG. 22 is a diagram illustrating an example of a force waveform.

In a third embodiment, as illustrated in FIG. 22, such a case is described, in which search has been started from the point PM and the slope of the force waveform after the characteristic change point is smaller than the slope before the characteristic change point, and thus a value smaller than 1 is respectively set as the left slope scaling factor SlpL and the right slope scaling factor SlpR. As the configurations of the inspecting device according to the third embodiment are identical to those of the first embodiment, the third embodiment is described while exemplifying constituent elements that are identical to those of the first embodiment and using like reference signs.

The inspection parameter designated by the inspection-parameter designation unit 9 includes the left slope scaling factor SlpL, the right slope scaling factor SlpR, and the approximate window distance d, as well as the designation of the point PM as in the first embodiment. The left slope scaling factor SlpL (first parameter) and the right slope scaling factor SlpR (first parameter) are both smaller than 1.

In the third embodiment, in the process at Step S27 included in the process for specifying the point SL as the rough change point (the process illustrated in FIG. 17), the characteristic-change-point recognition unit 82 determines whether the following mathematical expression (16) is satisfied instead of the mathematical expression (11).

$$ki \leq SlpL * km \quad (16)$$

If the mathematical expression (16) is not satisfied, the characteristic-change-point recognition unit 82 performs the process at Step S22 again. If the mathematical expression (16) is satisfied, the characteristic-change-point recognition unit 82 designates SL as i−k (Step S28) and finishes the process at Step S12.

In the process at Step S37 included in the process for specifying the point L as the characteristic change point on the basis of the point SL (the process illustrated in FIG. 19), the characteristic-change-point recognition unit 82 determines whether the following mathematical expression (17) is satisfied instead of the mathematical expression (13).

$$ki \geq km \quad (17)$$

If the mathematical expression (17) is not satisfied, the characteristic-change-point recognition unit 82 performs the process at Step S32 again. If the mathematical expression (17) is satisfied, the characteristic-change-point recognition unit 82 designates L as i (Step S38) and finishes the process at Step S13.

In this manner, according to the third embodiment, because the values of the left slope scaling factor SlpL and the right slope scaling factor SlpR are both set smaller than 1, the characteristic change point can be extracted from the force waveform, for example as illustrated in FIG. 22, in which the slope after the characteristic change point is smaller than the slope before the characteristic change point after search has been started by using the point PM as the point of the starting. With this configuration, the deformation start point or the deformation end point of the elastic component can be specified much easily.

When search is started by using the point PM as the point of the starting and the slope after the characteristic change point is larger than the slope before the characteristic change point, by setting a value larger than 1 as the slope scaling factor, the characteristic change point is specified; and by setting a value smaller than 1 as the slope scaling factor, the characteristic change point is not specified. Further, when the slope after the characteristic change point is smaller than the slope before the characteristic change point, by setting a value smaller than 1 as the slope scaling factor, the characteristic change point is specified; and by setting a value larger than 1 as the slope scaling factor, the characteristic change point is not specified. A user can, depending on the desired characteristic change point to specify, decide whether to set the slope scaling factor to a value larger than 1 or to a value smaller than 1.

The slope scaling factors can be each set independently on the left side and the right side. That is, a value larger than 1 can be set to one of the left slope scaling factor SlpL and the right slope scaling factor SlpR; and a value smaller than 1 can be set to the other factor.

The characteristic-change-point recognition unit 82 can determine whether the value set to the slope scaling factor is larger than 1 and can perform switching between execution of the operation described in the first embodiment and execution of the operation described in the third embodiment according to the determination result.

The inspection-parameter designation unit 9 can be configured so as to be able to specify two values, i.e., a value larger than 1 and a value smaller than 1 as the same slope scaling factor. The characteristic-change-point recognition unit 82 specifies the characteristic change point by using one slope scaling factor, and then it specifies the characteristic change point by using the other slope scaling factor, thereby enabling the characteristic change point to be specified, regardless of the magnitude of the slope right before or after the characteristic change point.

Fourth Embodiment

As the configurations of a fourth embodiment are identical to those of the first embodiment, the fourth embodiment is described while exemplifying constituent elements that are identical to those of the first embodiment and using like reference signs.

In the fourth embodiment, the inspection parameter designated by the inspection-parameter designation unit 9 includes designation of the point PM, the left slope scaling factor SlpL, the right slope scaling factor SlpR, the approximate window distance d, and an adjustment factor cl. In the process at Step S35 included in the process for specifying the point L as the characteristic change point on the basis of the point SL (the process illustrated in FIG. 19), the characteristic-change-point recognition unit 82 determines whether the following mathematical expression (18) is satisfied instead of the mathematical expression (12).

$$S(i+k)-S(i) \geq d' \tag{18}$$

It is assumed that d' is a value different from the approximate window distance d and is a positive real number. d' is defined by the following mathematical expression (19). Hereinafter, d' is referred to as search window length.

$$d'=cl*d \tag{19}$$

If the mathematical expression (18) is not satisfied, the characteristic-change-point recognition unit 82 performs the process at Step S34. If the mathematical expression (18) is satisfied, the characteristic-change-point recognition unit 82 calculates the slope of the approximate line of data having the data number i to data having the data number i+k (Step S36).

If cl is larger than 1 (for example, 2), an effect of reducing erroneous detection of termination conditions due to noise or the like (that is, determined as YES at Step S37) can be acquired with respect to the calculated slope ki. As cl increases, noise becomes stronger. However, if the number of pieces of data between search-accuracy characteristic change points at Step S13 is small, cl needs to be adjusted by a value larger than 1.

In contrast, if cl is smaller than 1 (for example, 0.5), an effect of accurately extracting the characteristic change point can be acquired under the condition where the noise has little effect.

In this manner, according to the fourth embodiment, by setting the variable search window length d', when there is much noise, erroneous detection can be reduced; and when there is less noise, the change point detection accuracy can be improved. Further, the accuracy of a physical characteristic (a slope) extracted by the inspecting device can be improved.

Fifth Embodiment

As the configurations of a fifth embodiment are equivalent to those of the first embodiment, the fifth embodiment is described while exemplifying constituent elements that are identical to those of the first embodiment and using like reference signs.

In the fifth embodiment, the inspection parameter designated by the inspection-parameter designation unit 9 further includes an adjustment factor SlpL2 (second parameter). In the process at Step S37 included in the process for specifying the point L as the characteristic change point on the basis of the point SL (the process illustrated in FIG. 19), the characteristic-change-point recognition unit 82 determines whether both of the following mathematical expressions (20) and (21) are satisfied instead of the mathematical expression (13).

$$ki \leq (1+SlpL2)*km \tag{20}$$

$$(1-SlpL2)*km \leq ki \tag{21}$$

If the mathematical expression (20) or (21) is not satisfied, the characteristic-change-point recognition unit 82 performs the process at Step S32 again. If both of the mathematical expressions (20) and (21) are satisfied, the characteristic-change-point recognition unit 82 designates L as i (Step S38), and the operation related to the process at Step S13 is finished.

The adjustment factor SlpL2, when the determination accuracy of the local slope is set, is set to be a real number from 0 to 1. Accordingly, the determination sensitivity of the final point L can be adjusted. Also at Step S15, it is possible to perform identical processes to adjust the determination sensitivity of the point R.

When deciding the final point L, the search detection sensitivity can be increased by using the method described above such that, if strictly matching accuracy is not required, a focus point that first satisfies a condition in which the local slope ki at a focus point reaches a range of the slope on the basis of the reference slope km and the adjustment factor SlpL2 as "second parameter" is specified as the point L.

In the descriptions of the first to fifth embodiments, the "process of deformation" refers to passage of time in a deformed state of an object formed of a single body or a plurality of objects with respect to a certain load, which is illustrated by using a force waveform. In the case of a plurality of objects, reaction forces generated by physical rigidity or a deformed state become complicated. A characteristic change point is set as a boundary in order to identify the reaction force. The characteristic change point is defined, for example, by a physical contact state, and when it is regarded that the rigidity is the same, the characteristic change point is addressed as the same state, and the boundary between these states can be referred to as the characteristic change point.

INDUSTRIAL APPLICABILITY

As described above, the inspecting device and the inspecting method according to the present invention are appropriately applied to an inspecting device and an inspecting method for inspecting characteristics of an elastic component that is in a state of being assembled to an assembled body.

REFERENCE SIGNS LIST

1 storage unit, 2 robot, 2a motor, 3 force acquisition unit, 3a force sensor, 4 hand, 5 position acquisition unit, 5a position sensor, 6 acquired-condition designation unit, 7 inspection-unit number selection unit, 8 inspection unit, 9 inspection-parameter designation unit, 10 inspection-range designation unit, 11 cutout unit, 12 inspection output unit, 13 display unit, 14 housing upper part, 15 movable contact point, 16 fixed contact point, 17 movable iron core, 17a movable iron-core central part, 18 plate, 19 magnetizing coil, 20 fixed iron core, 21 housing lower part, 22 push bar, 22a window, 23 contact spring, 24 movable contact, 25 tripping spring, 26 partial waveform, 27 window, 81 reference-characteristics calculation unit, 82 characteristic-change-point recognition unit, 83 characteristics calculation unit, 100 inspecting device, 200 electromagnetic contactor.

The invention claimed is:

1. An inspecting device comprising:
a force-waveform detection system that
applies a load to an assembled body having an elastic component assembled thereto in a direction of action of the elastic component and
acquires a force waveform describing a relation between the load and an amount of displacement;
a reception unit that receives an input of a designated point during a process of deformation of the elastic component in the force waveform acquired by the force-waveform detection system; and
an inspection unit that
calculates a local slope of the force waveform at the designated point,
calculates a local slope at a focus point different from the designated point, and
determines, on the basis of a comparison between the local slope at the focus point and the local slope at the designated point, whether the focus point is a change point of the force waveform, wherein
the inspection unit
searches for a first focus point that first satisfies, on the basis of the local slope at the designated point and a first parameter, a first condition at least stating that the local slope at the first focus point reaches a first threshold, while moving the first focus point in a direction away from the designated point by using the designated point as a point of the starting,
specifies the first focus point first satisfying the first condition as a first change point,
searches for a second focus point that first satisfies, on the basis of a second parameter, a second condition at least stating that the local slope at the second focus point reaches the local slope at the designated point or is inside of a range between the local slope at the designated point and the slope, while moving the second focus point in a direction approaching the designated point by using the first change point as a point of the starting, and
specifies the second focus point first satisfying the second condition as a second change point.

2. The inspecting device according to claim 1, wherein the first condition further states that a difference of loads, which are pieces of data at opposite ends in the force waveform in a preset range that includes the first focus point, exceeds a third parameter.

3. The inspecting device according to claim 1, wherein the first threshold is a value obtained by multiplying the local slope at the designated point with the first parameter.

4. The inspecting device according to claim 1, wherein the range of the slope, on the basis of the local slope at the designated point and the second parameter, is
from a value obtained by multiplying the local slope at the designated point by a value obtained by subtracting the second parameter from 1
to a value obtained by multiplying the local slope at the designated point with a value obtained by adding the second parameter to 1.

5. The inspecting device according to claim 1, wherein the inspection unit
specifies two second change points having the designated point sandwiched therebetween, and
calculates an elastic force of the elastic component at an arbitrary position on the basis of a force waveform between the two second change points.

6. The inspecting device according to claim 1, wherein the inspection unit
specifies two second change points having the designated point sandwiched therebetween, and
calculates a modulus of elasticity of the elastic component on the basis of a force waveform between the two second change points.

7. An inspecting method executed by an inspecting device including a force-waveform detection system, a reception unit, and an inspection unit, the inspecting method comprising:
a first step at which the force-waveform detection system
applies a load to an assembled body having an elastic component assembled thereto in a direction of action of the elastic component, and
acquires a force waveform describing a relation between the load and an amount of displacement;
a second step at which the reception unit receives an input of a designated point during a process of deformation of the elastic component in the force waveform acquired by the force-waveform detection system; and
a third step at which the inspection unit
calculates a local slope of the force waveform at the designated point,
calculates a local slope at a focus point different from the designated point, and determines, on the basis of a comparison between the local slope at the focus point and the local slope at the designated point, whether the focus point is a change point of the force waveform, wherein the third step includes a step of searching for a first focus point that first satisfies, on the basis of the local slope at the designated point and a first parameter, a first condition that at least states that the local slope at the first focus point reaches a first threshold, while moving the first focus point in a direction away from the designated point by using the designated point as a point of the starting, thereby specifying the first focus point first satisfying the first condition as a first change point, and a step of searching for a second focus point that first satisfies, on the basis of a second parameter, a second condition that at least states that the local slope at the second focus point reaches the local slope at the designated point or is inside of a range between the local slope at the designated point and the slope, while moving the second focus point in a direction approaching the designated point by using the first change point as a point of the starting, thereby specifying the second focus point first satisfying the second condition as a second change point.

* * * * *